(12) United States Patent
Todokoro et al.

(10) Patent No.: US 7,049,591 B2
(45) Date of Patent: May 23, 2006

(54) SCANNING ELECTRON MICROSCOPE

(75) Inventors: Hideo Todokoro, Hinode (JP); Makoto Ezumi, Mito (JP); Yoichi Ose, Mito (JP); Naomasa Suzuki, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 12 days.

(21) Appl. No.: 11/016,849

(22) Filed: Dec. 21, 2004

(65) Prior Publication Data
US 2005/0133719 A1    Jun. 23, 2005

Related U.S. Application Data

(63) Continuation of application No. 10/643,892, filed on Aug. 20, 2003, now Pat. No. 6,847,038, which is a continuation of application No. 10/069,571, filed on Jul. 15, 2002, now Pat. No. 6,646,262.

(51) Int. Cl.
*H01J 37/20* (2006.01)

(52) U.S. Cl. ........................... 250/310; 250/305

(58) Field of Classification Search ................ 250/310, 250/305, 306, 307
See application file for complete search history.

(56) References Cited

U.S. PATENT DOCUMENTS

| | | |
|---|---|---|
| 4,554,455 A | 11/1985 | Todokoto et al. |
| 5,118,941 A | 6/1992 | Larson |
| 5,389,787 A | 2/1995 | Todokoro et al. |
| 5,493,116 A | 2/1996 | Toro-Lira et al. |
| 5,608,218 A | 3/1997 | Sato et al. |
| 5,872,358 A | 2/1999 | Todokoro et al. |
| 6,043,491 A | 3/2000 | Ose et al. |
| 6,091,249 A | 7/2000 | Talbot et al. |
| 6,583,414 B1 * | 6/2003 | Nozoe et al. ............. 250/310 |
| 6,646,262 B1 | 11/2003 | Todokoro et al. |
| 6,667,476 B1 | 12/2003 | Todokoro et al. |
| 6,946,656 B1 * | 9/2005 | Ezumi et al. ............. 250/310 |

FOREIGN PATENT DOCUMENTS

| | | |
|---|---|---|
| EP | 853243 | 7/1998 |
| JP | 10-313027 | 11/1998 |
| WO | WO 99/46798 | 9/1999 |

* cited by examiner

*Primary Examiner*—Kiet T. Nguyen
(74) *Attorney, Agent, or Firm*—Dickstein Shapiro Morin & Oshinsky LLP

(57) ABSTRACT

A scanning electron microscope with an energy filter which can positively utilize secondary electrons and/or reflected electrons which collide against a mesh electrode and are lost. The scanning electron microscope which has a porous electrode for producing an electric field for energy-filtering electrons produced by applying a primary electron beam to a sample and a 1st electron detector which detects electrons passing through the porous electrode is characterized by further having a porous structure provided near the sample, a deflector which deflects electrons from the axis of the primary electron beam, and a 2nd electron detector which detects the electrons deflected by the deflector.

9 Claims, 16 Drawing Sheets

FIG.13
a) IMAGE OBTAINED FROM FIRST ELECTRON DETECTOR
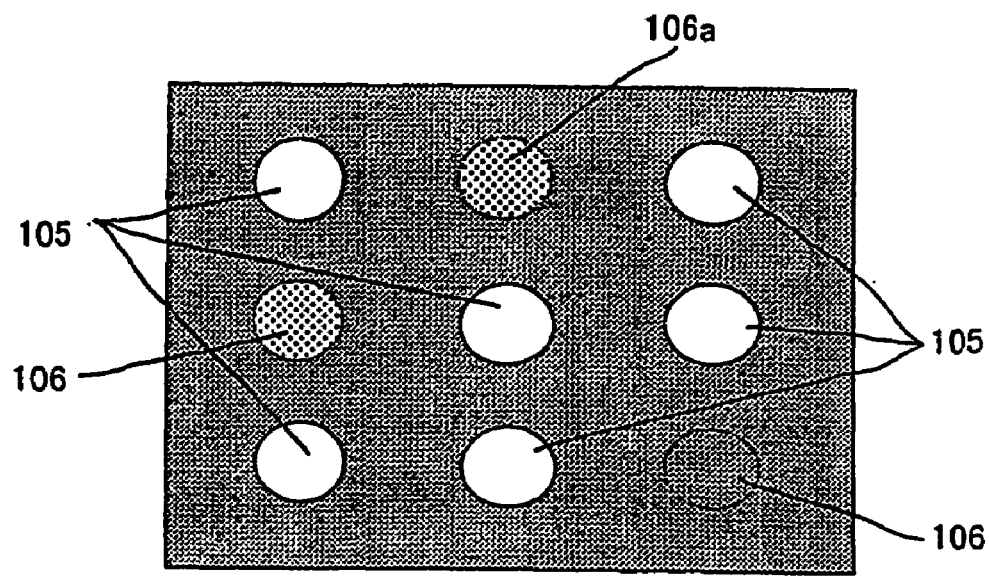
b) IMAGE OBTAINED FROM SECOND ELECTRON DETECTOR
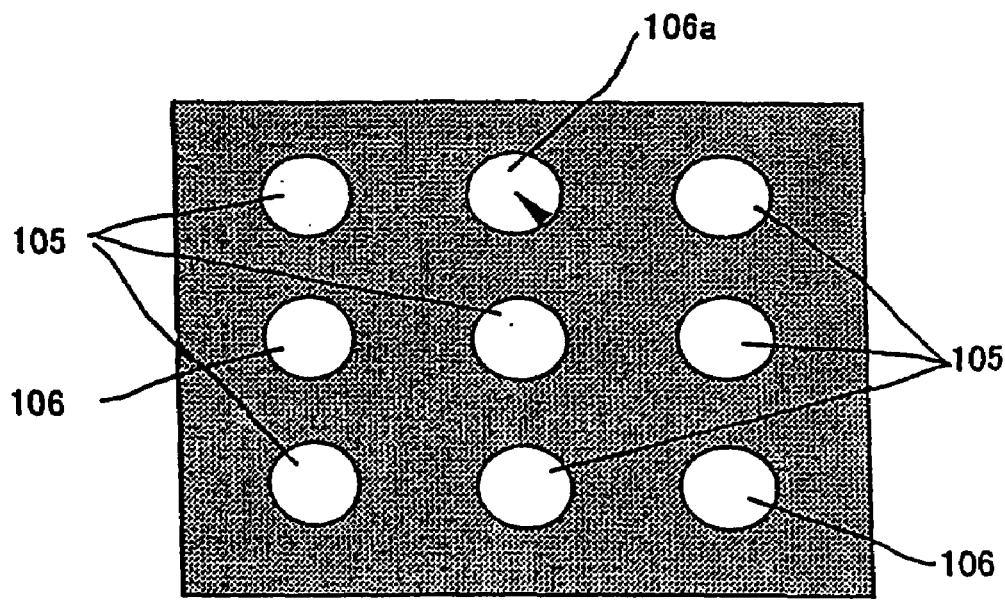

SCANNING ELECTRON MICROSCOPE

CROSS REFERENCE TO RELATED APPLICATIONS

The present application is a continuation of U.S. application Ser. No. 10/643,892, filed Aug. 20, 2003, now U.S. Pat. No. 6,847,038 which in turn is a continuation of U.S. application Ser. No. 10/069,571, filed Jul. 15, 2002 (now U.S. Pat. No. 6,646,262, issued Nov. 11, 2003), the disclosures of which are herewith incorporated by reference in their entirety.

TECHNICAL FIELD

This invention relates to an electron microscope, and in particular to a scanning electron microscope which is suitable for use in observation, inspection, or measurement of semiconductors.

BACKGROUND ART

Scanning electron microscopes have long been used to inspect or observe semiconductor devices. Among such scanning electron microscopes, there are electron beam testers in which electrons obtained from the sample are energy-discriminated, an electric potential contrast image is created based on discriminated electrons, and inspections are performed for defects in the wiring of semiconductor devices. Japanese Patent Laid-open No. 10-313027 discloses an electron beam tester and a method of wiring defect inspection using this electron beam tester.

The above patent publication discloses a technique for judging whether a specific site of the sample is electrically isolated, by static electrification of the sample and confirmation of the extent of static charge in the electrified region.

DISCLOSURE OF THE INVENTION

If a specific member (such as wiring) on the sample is electrically isolated from other members, as a result of the above static electrification, electric charge accumulates in this specific member. On the other hand, if the specific member is electrically grounded, there is no accumulation of static charge. By observing this static charge state, it is possible to judge, for example, whether wiring has been broken.

The above reference discloses a method in which, by intentionally applying static charge to the sample surface, and using a charged particle beam device comprising an energy filter to observe electric potential contrasts, breaks and defects in electric wiring or similar formed on the sample surface are inspected. However, there is the following problem.

In general, by applying a certain negative voltage to a mesh-shape electrode, the energy filter used in a scanning electron microscope selectively detects electrons having a higher acceleration voltage than the applied voltage. However, a mesh-shape electrode is physically large, and so among the secondary electrons or reflected electrons which are generated or reflected by the sample, there are electrons which collide with this mesh-shape electrode. Although these electrons carry information about the sample, they are lost without being detected.

The present invention is intended to resolve this problem, and has as an object the effective utilization of secondary electrons and/or reflected electrons which collide with a mesh-shape electrode and are lost in a scanning electron microscope comprising an energy filter.

In order to achieve the above object, the present invention provides a scanning electron microscope comprising an electron source, a focusing lens which focuses a primary electron beam emitted from the electron source, a porous electrode to form an electric field which performs energy filtering of electrons obtained as a result of irradiation of the above sample by the above primary electron beam, focused by the focusing lens, and a first electron detector which detects electrons passing through the porous electrode; characterized in further comprising a porous structure positioned closer to the above sample than the above porous electrode, a deflector positioned closer to the above sample than to the porous structure and which deflects electrons away from the axis of the above primary electron beam, and a second electron detector which detects electrons deflected by the deflector.

Secondary electrons and reflected electrons which collide with the porous structure generate secondary electrons as a result of the collision. In this invention, by using a second electron detector to detect the secondary electrons, it becomes possible to use in inspections and measurements the electrons which collide with the energy filter, and which previously could not be detected.

This invention makes possible various observations, inspections and measurements which heretofore could not be performed, based on the secondary electrons detected by this second electron detector.

BRIEF DESCRIPTION OF THE DRAWINGS

FIG. 13 is a figure showing an example of an output image of the device of an embodiment of this invention;

BEST MODE FOR CARRYING OUT THE INVENTION

Below embodiments of this invention are explained, using the drawings to aid understanding of the invention.

When using a scanning electron microscope to observe the processed shape of a wafer in a semiconductor manufacturing process, in order to avoid unstable negative static electrification of insulators within the wafer due to electron irradiation, it is desirable that observations be performed using low accelerating voltages of less than 2 kV. The reason for selecting a low accelerating voltage is related to the secondary electron emission efficiency (δ) arising when a substance is irradiated with electrons.

Figure 1:
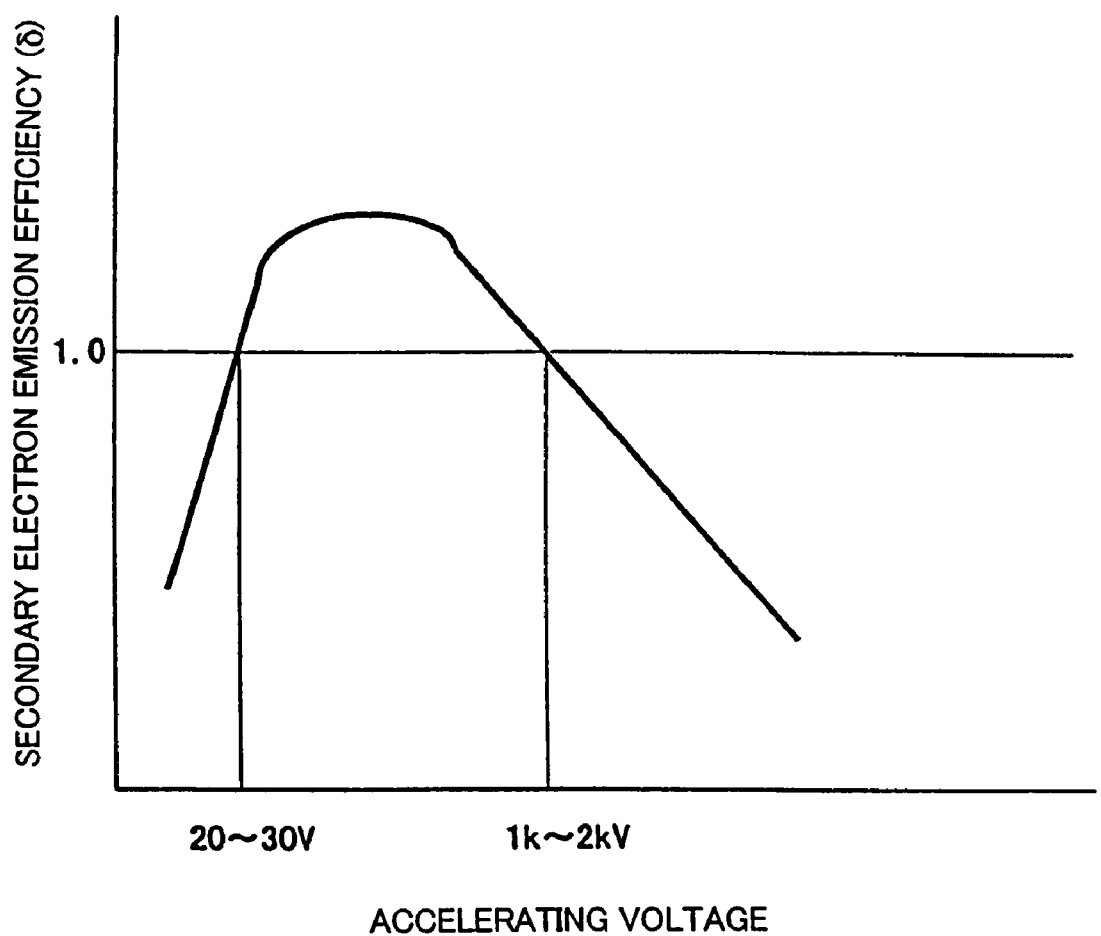
FIG. 1 is a figure which explains the accelerating voltage dependence of the secondary electron emission efficiency $\delta$.

The secondary electron emission efficiency (δ) is defined as the ratio (quantity of secondary electrons)/(quantity of incident electrons). FIG. 1 shows the relation between the secondary electron emission efficiency (δ) and the accelerating voltage. If an accelerating voltage is selected such that the secondary electron emission efficiency (δ) is 1.0, then the number of electrons entering (incident electrons) and the number of electrons leaving (secondary electrons) are equal, and so static electrification does not occur even in the case of insulating material. The accelerating voltage at which this δ is 1.0 varies with the substance, but is within the range of accelerating voltages between 1 and 2 kV.

In the high accelerating voltage range at which the secondary electron emission efficiency (δ) is less than 1.0 (the accelerating voltages of ordinary scanning electron microscopes are from 5 kV to 30 kV, in this range), the number of entering electrons is large, and so negative static electrification occurs. When the sample undergoes negative static electrification, incident electrons are decelerated by the electric field created by the negative static electrification. Due to deceleration, there is an equivalent reduction in the accelerating voltage of the incident electrons.

This negative static electrification proceeds until the secondary electron emission efficiency (δ) for the equivalent accelerating voltage becomes 1.0. For example, at an accelerating voltage of 10 kV, if the negative static electrification of the sample does not reach 8 kV or higher, the secondary electron emission efficiency (δ) for the equivalent accelerating voltage will not become 1.0. When such a large negative static electrification occurs, discharge within the sample, and anomalous deflection of incident electrons by the electric field created by the negative static electrification occur, and accurate observation becomes impossible.

On the other hand, in accelerating voltage ranges for which the secondary electron emission efficiency (δ) exceeds 1.0 (low accelerating voltages), secondary electron emission (electrons leaving) is more numerous, and so the surface of insulators is positively electrified. The electric field created by the positive electrification accelerates primary electrons; but the electric field created by positive electrification acts to pull back secondary electrons. Because the energy of secondary electrons is low, at several eV, if the sample is positively electrified to several volts, secondary electrons are pulled back. That is, the pulling-back of secondary electrons causes positive static electrification to stop and stabilize at an equivalent secondary electron emission efficiency (δ) of 1.0.

This positive static electrification is several volts, and is stable, and so does not interfere with scanned image observations. Hence in observations of semiconductor wafers containing insulators, generally low accelerating voltages from 500 V to 1000 V, at which the secondary electron emission efficiency (δ) of insulators which are to be observed exceeds 1.0, are selected. It is desirable that semiconductor wafers containing insulators be observed under conditions such as these.

Figure 2:
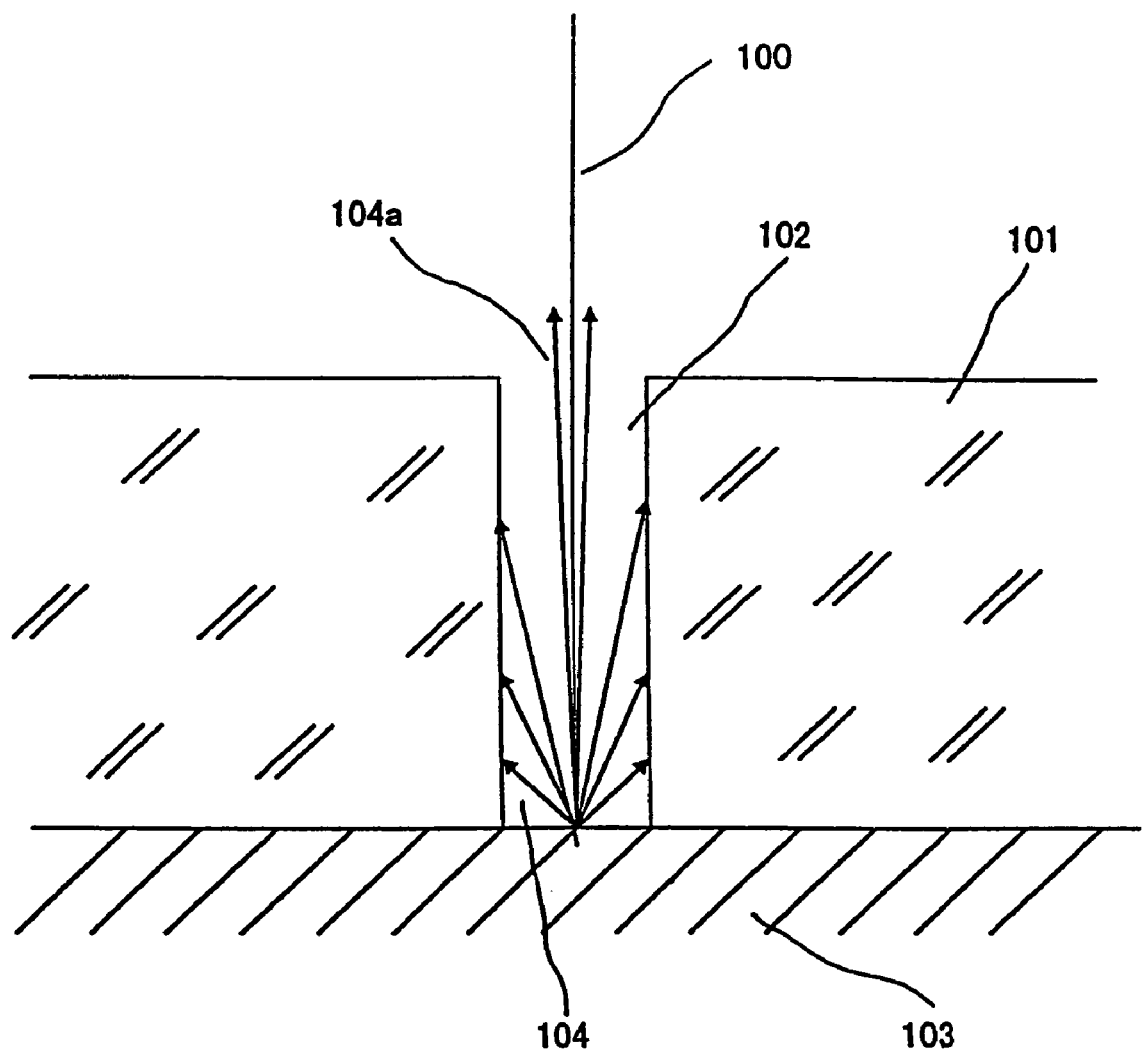
FIG. 2 is a figure showing collisions of secondary electrons within a deep contact hole.

However, one problem with observations of very finely shaped semiconductor objects is that of observing deep (high aspect ratio) contact holes. FIG. 2 shows the cross-sectional structure of a contact hole. The purpose of this contact hole 102 is to enable formation of contact wiring between layers, for electrical connections between the conductor substrate 103 and wiring (not shown) formed on the insulator 101. The purpose of observation is to confirm the presence of the aperture of the contact hole 102 formed by etching the insulator 101.

If insulating material remains at the bottom of the contact hole, and the conductor substrate 103 is not exposed, then even if the hole is filled with a metal (deposition), connection with the conductor substrate 103 will not be possible and a connection fault will result. Hence there is a need use a scanning electron microscope to observe the bottom of the contact hole 102 and confirm that the substrate 103 is exposed.

However, as shown in the figure, most of the secondary electrons 104 emitted at the bottom of the contact hole 102 due to irradiation of primary electrons 100 collide with the walls of the contact hole 102 and are lost. Only the portion of the secondary electrons directed upward 104a escape from the contact hole 102. In cases where the contact hole is shallow (with an aspect ratio of 1 to 2 or less), a substantial portion of the secondary electrons escape from the contact hole 102, and so observation is possible. But when, as in the most recent semiconductor devices, smaller dimensions are adopted and the aspect ratio exceeds 3, observation of the bottom of the contact hole 102 becomes impossible.

Figure 3:
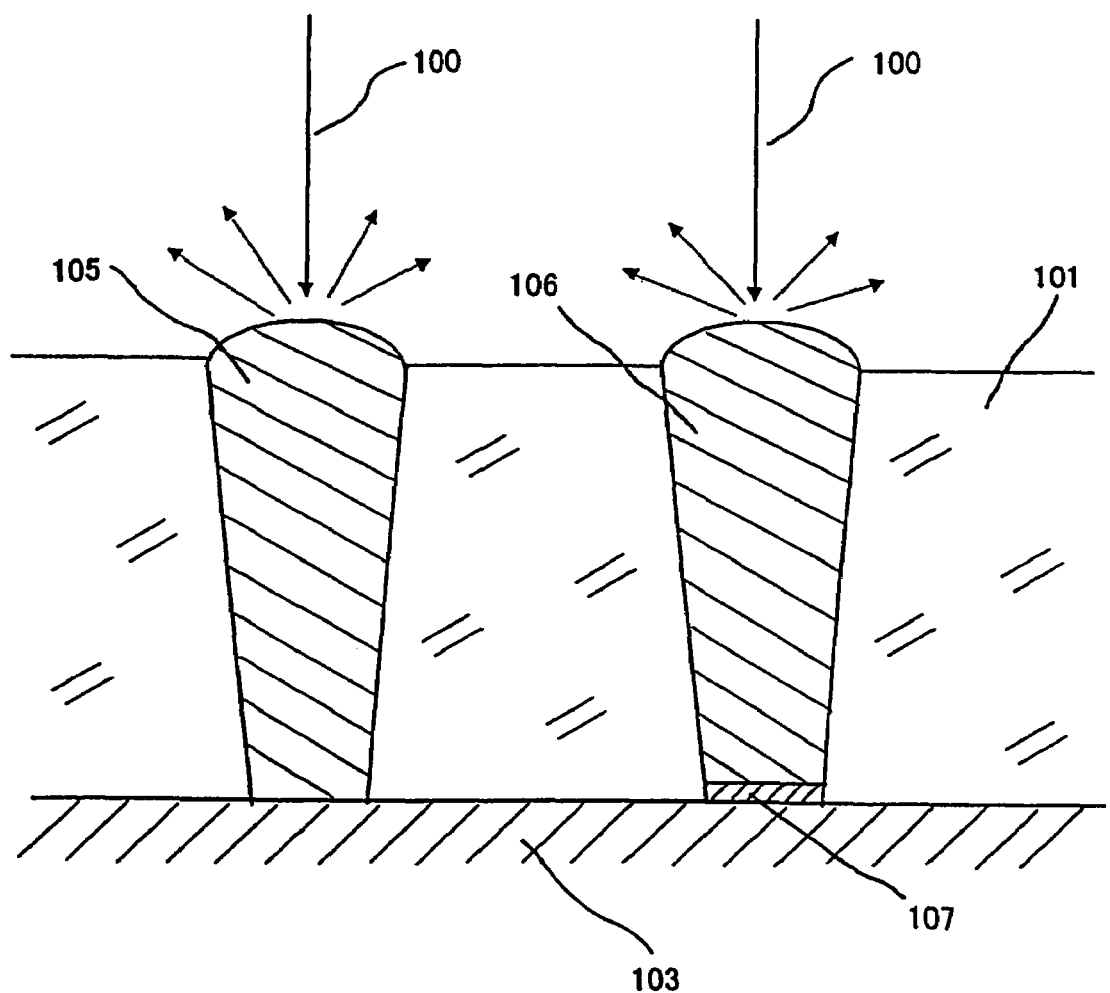
FIG. 3 is a figure showing the state of insulation of contact wiring.

FIG. 3 shows an example in which judgment using a scanning electron microscope is similarly difficult. This is a state in which the contact hole of FIG. 2 is filled with metal (for example, copper), and contact wiring 105, 106 has been formed connecting the conductor substrate 103 and the upper wiring (not shown). A normal electrical connection is obtained between the contact wiring 105 and the conductor substrate 103. Because an insulating film 107 remains at the bottom of the hole in the contact wiring 106, although the external appearance is the same, an electrical contact is not obtained. When the contact wiring 106 is observed from above with a scanning electron microscope device, there is no apparent change from the case of the contact wiring 105, and it is difficult to detect a connection fault.

The above-described problem can be resolved by: [1] employing observation conditions in which positive static charge is applied to the insulator surface; [2] performing energy filtering, in which energy differences of secondary electrons are separated and detected; and, [3] appropriately setting a threshold for the separation energy for this energy filtering.

Of these, [1] "observation conditions involving application of positive charge" is as follows.

Figure 4:
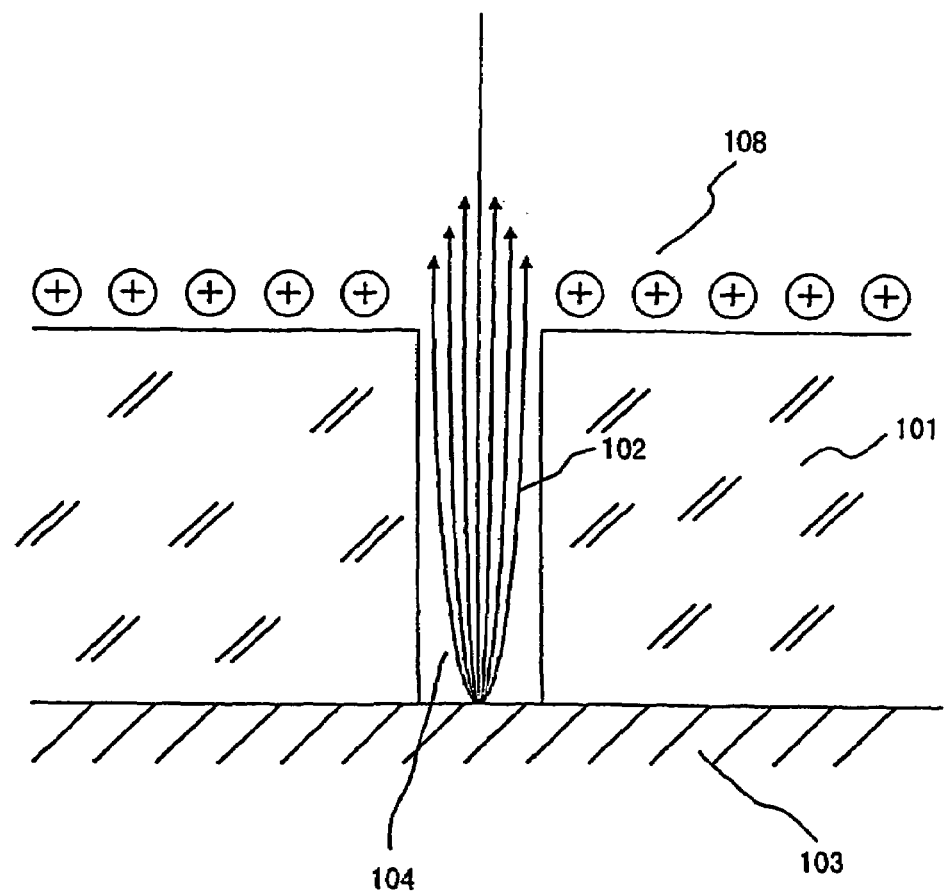
FIG. 4 is a figure showing positive electrification to realize observation of a contact hole with a high aspect ratio.

First, as one example, in observing the high-aspect ratio hole of FIG. 2, an accelerating voltage for which δ>1.0 is selected. As explained above, by selecting this accelerating voltage, positive static charge 108 can be applied to the surface of the insulator 101, as shown in FIG. 4.

Figure 5:
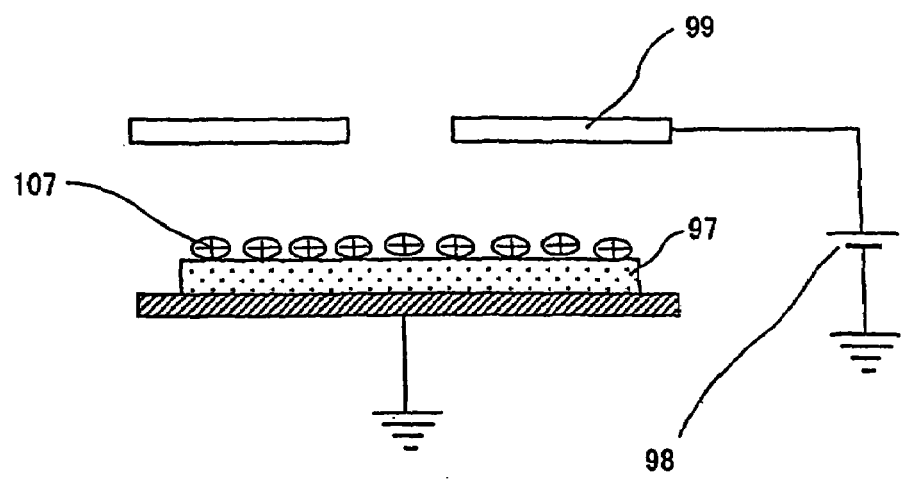
FIG. 5 is a figure showing another example of electrification of a sample surface.

In order to apply a positive charge to the surface of an insulator 101, it is possible to apply, at the sample surface, an electric field (reverse electric field) which suppresses the pulling-back of secondary electrons, emitted from the surface, by the electric field created by positive charge at the surface of the insulator 101. As shown in FIG. 5, an opposing substrate is provided which opposes the sample (insulator) 97, and a positive voltage (control voltage) 98 is applied to this electrode. As a result, an electric field is created at the insulator surface which pulls secondary electrons toward the control electrode 99, so that pulling-back of secondary electrons by the electric field created by positive charge is suppressed, and the positive charge 107 is stabilized.

In order to observe the bottom of a contact hole 102 like that in FIG. 2, electrification through selection of the accelerating voltage alone is insufficient. This is because electrification through selection of the accelerating voltage only creases a charged state of several volts, which is insufficient to pull out secondary electrons in the contact hole 102. In order to observe contact holes with a high aspect ratio, more intense positive electrification must be applied.

To do so, a member corresponding to the above-described opposing electrode 99 is provided, and higher positive electrification is created. Through an electrification method employing this opposing electrode 99, electrification on the order of several tens of volts can be created. If electrification of for example 10 V is created between the conductor substrate 103 and the surface of the insulator 101 in FIG. 4, an electric field as strong as 100 kV/cm (assuming the thickness of the insulator 101 to be 1 μm) is formed; secondary electrons 104 created at the bottom of the contact hole 102 are focused by the electric field as shown in FIG. 4, and can exit from the aperture of the contact hole 102.

In order to observe the contact wiring 105, 106 as well as the bottom of the contact hole 102 using a scanning electron microscope 1, it is desirable that the accelerating voltage be set to 20 eV or above and less than 2 keV, at which, as explained above, the secondary electron emission efficiency δ is 1 or greater, and that a member corresponding to the opposing electrode 99 be provided.

Next, the energy filtering to separate and detect energy differences in secondary electrons of [2] is explained. An energy filter generally has a mesh-shape electrode. In the case of a device to detect electrons, such as a scanning electron microscope, either a negative voltage is applied to the mesh-shape electrode, or else a decelerating electric field for secondary electrons headed toward the electron detector is formed between the mesh-shape electrode and another member, to selectively admit and detect secondary electrons having energy equal to or greater than a certain constant energy.

In this invention, by appropriately setting a negative voltage applied to the mesh-shape electrode or a decelerating electric field, it is possible to judge accurately whether the contact wiring 105 and 106 is defective or not. In this embodiment, energy filtering is performed using a mesh-shape electrode, but this invention is not limited to such a configuration, and another means of forming a decelerating electric field which decelerates secondary electrons and reflected electrons heading toward the detection surface of the electron detector may be used instead.

Figure 6:
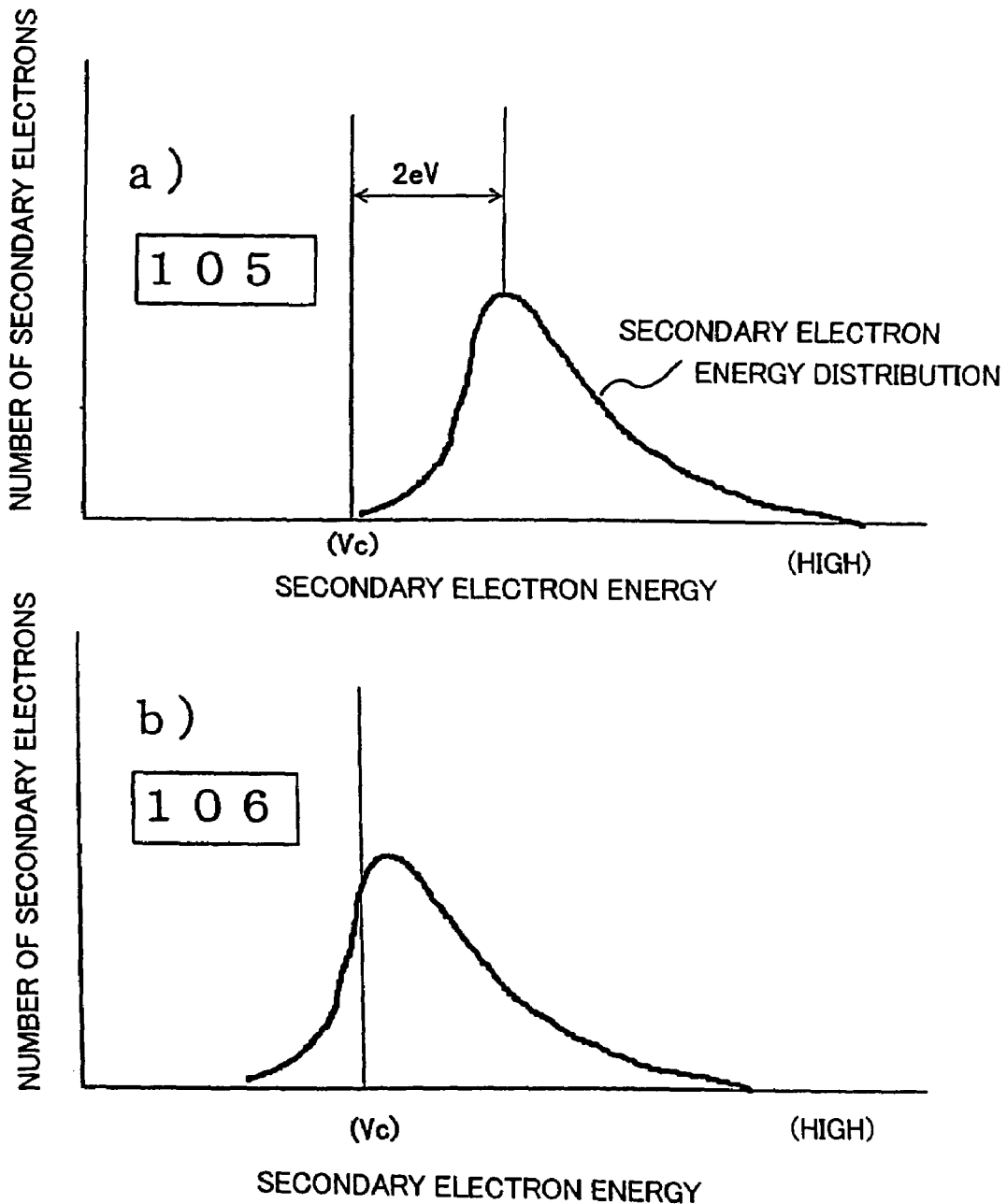
FIG. 6 is a figure showing the energy distribution of secondary electrons emitted from contact wiring.

Next, the separation energy threshold setting of the energy filter in [3] is explained. It was already explained that the total numbers of secondary electrons emitted from the contact wiring 105 and 106 are the same. However, differences occur in the energies of the secondary electrons. This is explained using FIG. 6.

The horizontal axis indicates the energy, as a voltage, of secondary electrons at the point of passing through the opposing electrode 99. Vc is the control voltage 98 applied to the opposing electrode 99. Here (a) shows the energy distribution of secondary electrons emitted from normal contact wiring 105. The energy distribution of the secondary electrons has a maximum value at approximately 2 V. Hence the distribution of the secondary electrons is to the right of the reference voltage Vc (if the sample is grounded, 0 V) in which the sample is placed.

On the other hand, (b) is an example of contact wiring 106 with a connection fault. Due to the connection fault, the contact wire is positively electrified, similarly to the insulator. Because of this, the energy distribution of secondary electrons is shifted to the left by the amount of the positive electrification. If this energy difference (distribution difference) could be detected, normal contact wiring 105 could be discriminated from contact wiring 106 with a connection fault. In this embodiment, the separation energy threshold value of the energy filter is set such that this energy difference can be detected.

Specifically, the voltage applied to the energy filter is adjusted such that the passage of electrons having that energy (Vc) at which the number of electrons obtained from the contact wiring 106 is maximum is suppressed, while electrons having that energy (Vc+2 eV) at which the number of electrons obtained from the contact wiring 105 is maximum are allowed to pass.

In the above explanation, the sample surface, including contact wiring, is positively electrified, and contact wiring is judged to be faulty or not according to the condition of charge. More specifically, focusing on the fact that contact wiring for which electrical connection with the conductor substrate is incomplete and contact wiring which is correctly connected electrically will have different charge states, the electron energy difference arising from this difference in charge states is utilized to judge whether the connection of contact wiring is faulty.

Figure 7:
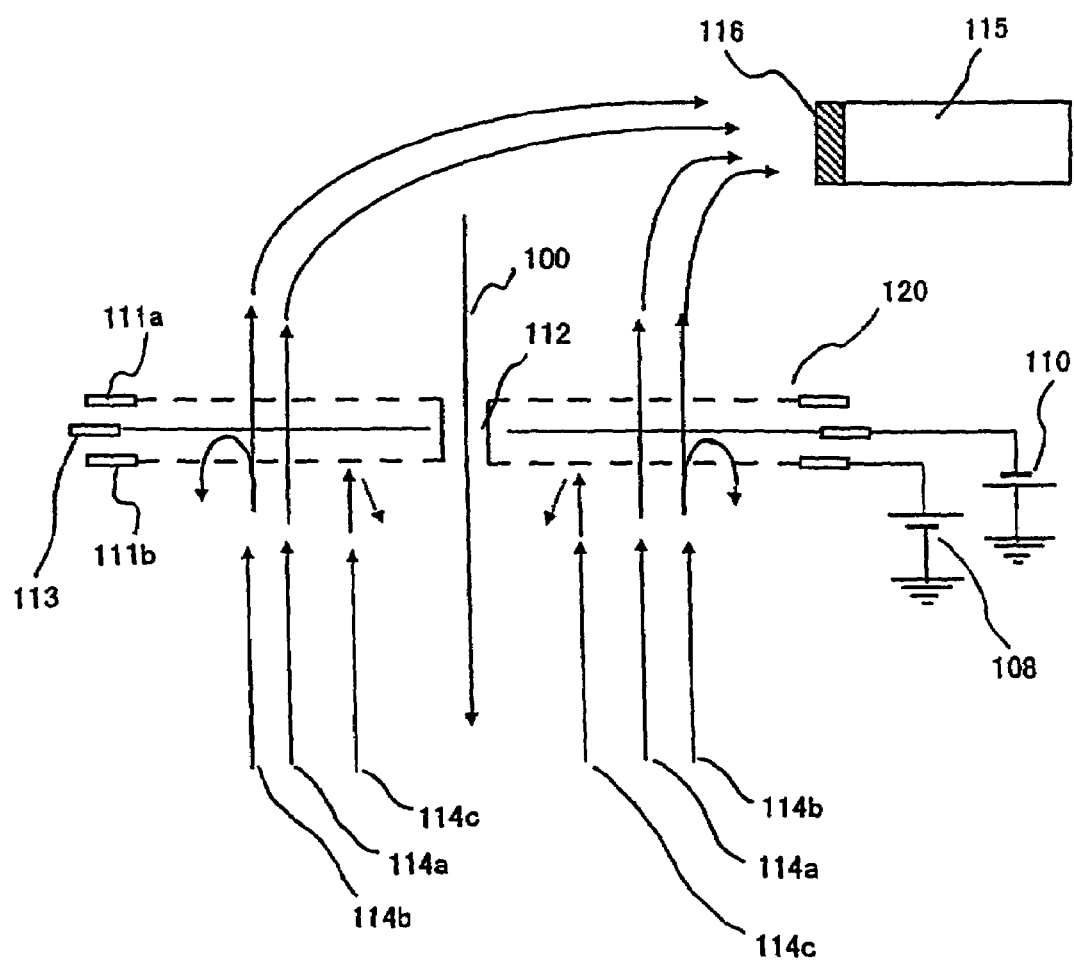
FIG. 7 is a figure showing in summary an energy filter.

FIG. 7 shows the basic configuration of an energy filter. This shows an example of the placement of an energy filter 120 in the position of the opposing electrode 99 of FIG. 5. The energy filter 120 comprises shield mesh 111(a) (b), and filter mesh 113, which is one type of porous electrode. An aperture 112 allowing the passage of the primary electron beam is provided in the energy filter 120.

A control voltage 108 is applied to the shield mesh 111a, 111b, to accelerate the secondary electrons 114a, 114b, 114c. 115 is a secondary electron detector; secondary electrons which have passed through the energy filter 120 are absorbed by a scintillator 116 to which a positive voltage (for example, 10 kV) is applied, and are detected (the details of the detector are explained in an embodiment).

Here, the case in which the filter voltage 110 is set to 0 V is considered (the sample is at ground potential). For example, even if secondary electrons (114a) emitted from the contact wiring 105 shown in FIG. 3 are decelerated by the 0 V of the filter voltage 110 applied to the filter mesh 113, all secondary electrons (the obliquely shaded portion of a) in FIG. 8) pass through the energy filter 120 and are detected by the secondary electron detector 115.

Figure 8:
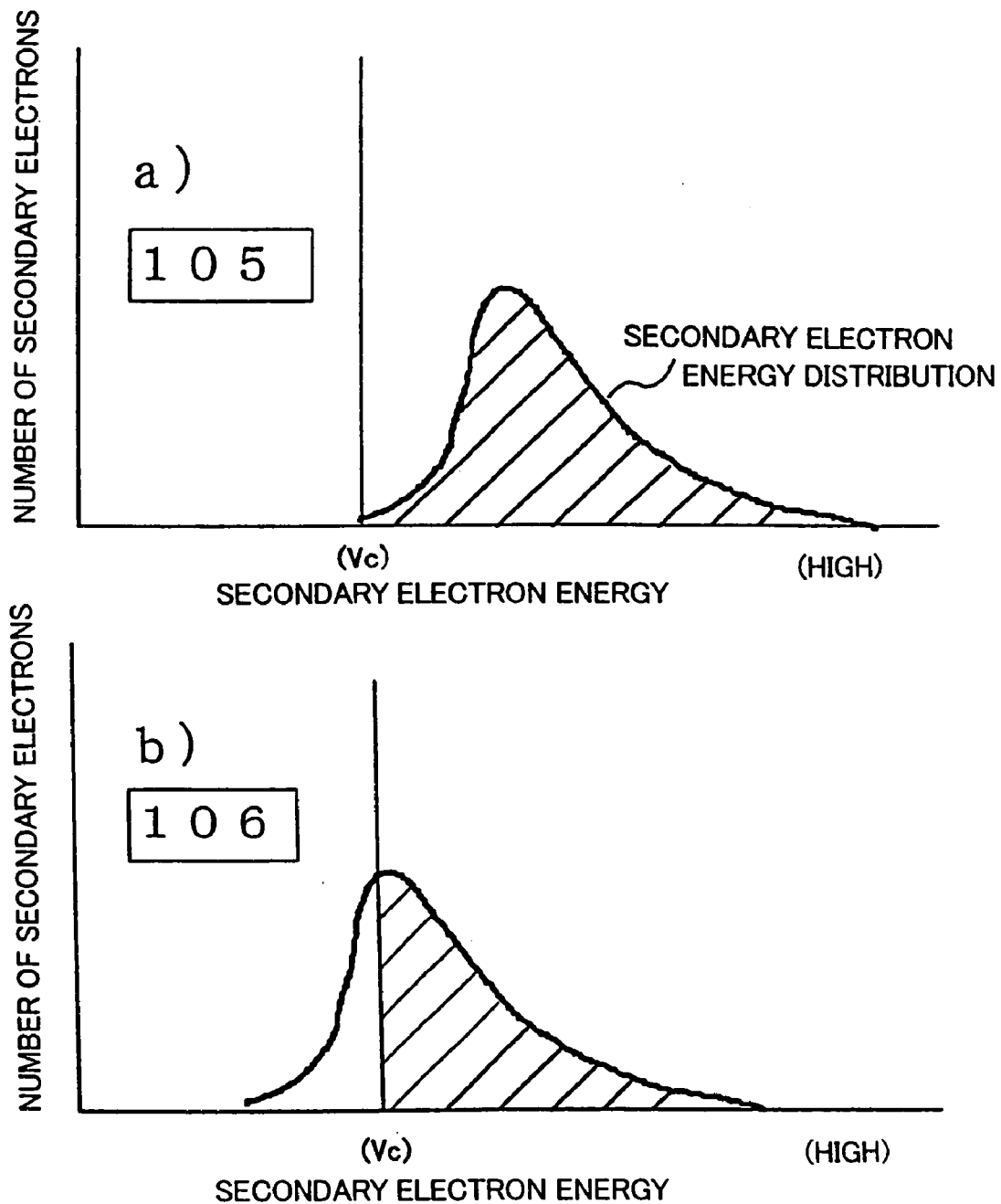
FIG. 8 is a figure showing the effect of an energy filter.

On the other hand, of the secondary electrons (114b) emitted from the contact wiring 106 shown in FIG. 3, only those secondary electrons with high energies (the obliquely shaded portion of b) in FIG. 8) pass through the energy filter 120 and are detected. Thus by providing such an energy filter, connection faults which previously could not be detected can be detected as differences in brightness.

The secondary electrons 114c shown in FIG. 7 are secondary electrons that have collided with the shield mesh 111b. The mesh transmission ratio is at best approximately 80%, and when three meshes are stacked, as in this example, is about 50%. When an energy filter is used, it is seen that the efficiency of use of secondary electrons worsens.

Figure 9:
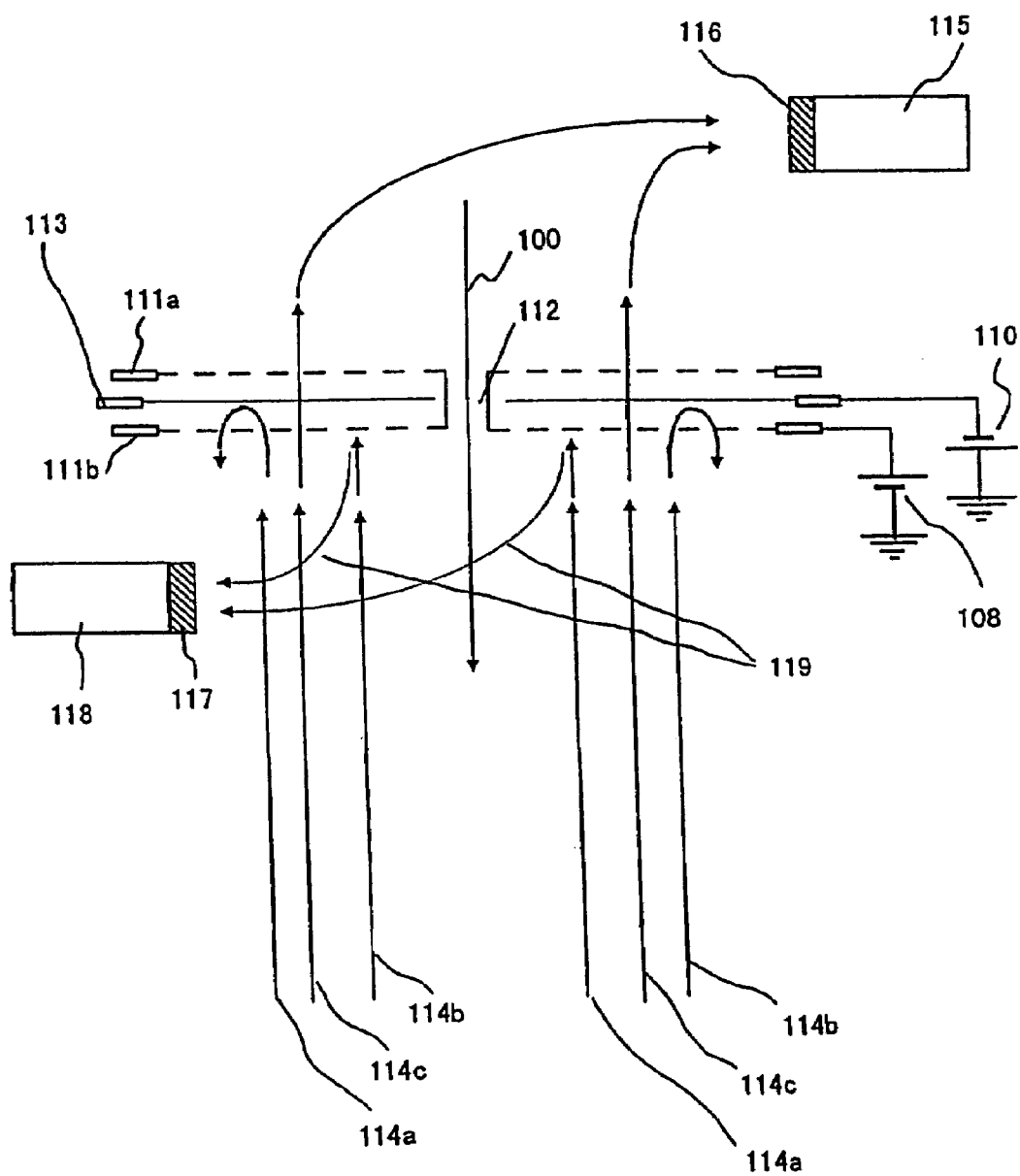
FIG. 9 is a figure showing the energy filter of an embodiment of this invention.

The device of the embodiment explained below focuses on this point. FIG. 9 shows a configuration which can achieve improved efficiency of use of secondary electrons.

In the device of this embodiment of the invention, in order to obtain information based on electrons colliding with the energy filter which previously could not be detected, a second electron detector (secondary electron detector 118) is positioned on the sample side (the side from which secondary electrons originate) of the energy filter. This second electron detector detects secondary electrons 119 generated from the shield mesh 111b by means of electrons colliding with the shield mesh 111b.

These secondary electrons have information specific to secondary electrons and reflected electrons obtained from the sample, and so, in effect, electrons colliding with the shield mesh 111b are detected. By means of such a configuration, electrons which previously were lost can be effectively utilized.

In the device of this embodiment of the invention, the electron transmission ratio of the shield mesh 111b is 50%. The thickness of the ribs of the mesh is set such that the transmission ratio of the shield mesh 111b is 50%, and a filter mesh 113 with transmission ratio of 80% and shield mesh 111a are positioned so as to overlap with this mesh, so that overall the transmission ratio is 50%.

The shield mesh 111b is a porous structure; it is desirable that the shield mesh 111b be formed from gold, platinum, or some other conductive material with a high secondary electron emission efficiency, or from members covered with these conductive materials. In order to generate secondary electrons from these conductive members, the secondary electrons 114 must be collided with the mesh using an accelerating voltage of approximately a certain magnitude. In the explanation of FIG. 9, the control voltage 108 is made 100 V or higher to impart an accelerating energy to the secondary electrons 114; but this invention is not limited to this method. Other methods are discussed below. It is effective to set this secondary electron accelerating voltage to a value such that the secondary electron emission efficiency shown in FIG. 1 exceeds 1.0.

The following explanation is for a case in which the transmission ratio of the shield mesh 111b is 50%; however, the transmission ratio is not thus limited, and should be selected appropriately according to the purpose of observation and other factors. Also, it is desirable that the shield mesh 111b be positioned so as to have a two-dimensional extension in directions intersecting with the axis of the primary electron beam. Further, if the effect on the primary electron beam is taken into consideration, it is desirable that the shield mesh 111b be formed in directions perpendicular to the primary electron beam.

Figure 10:
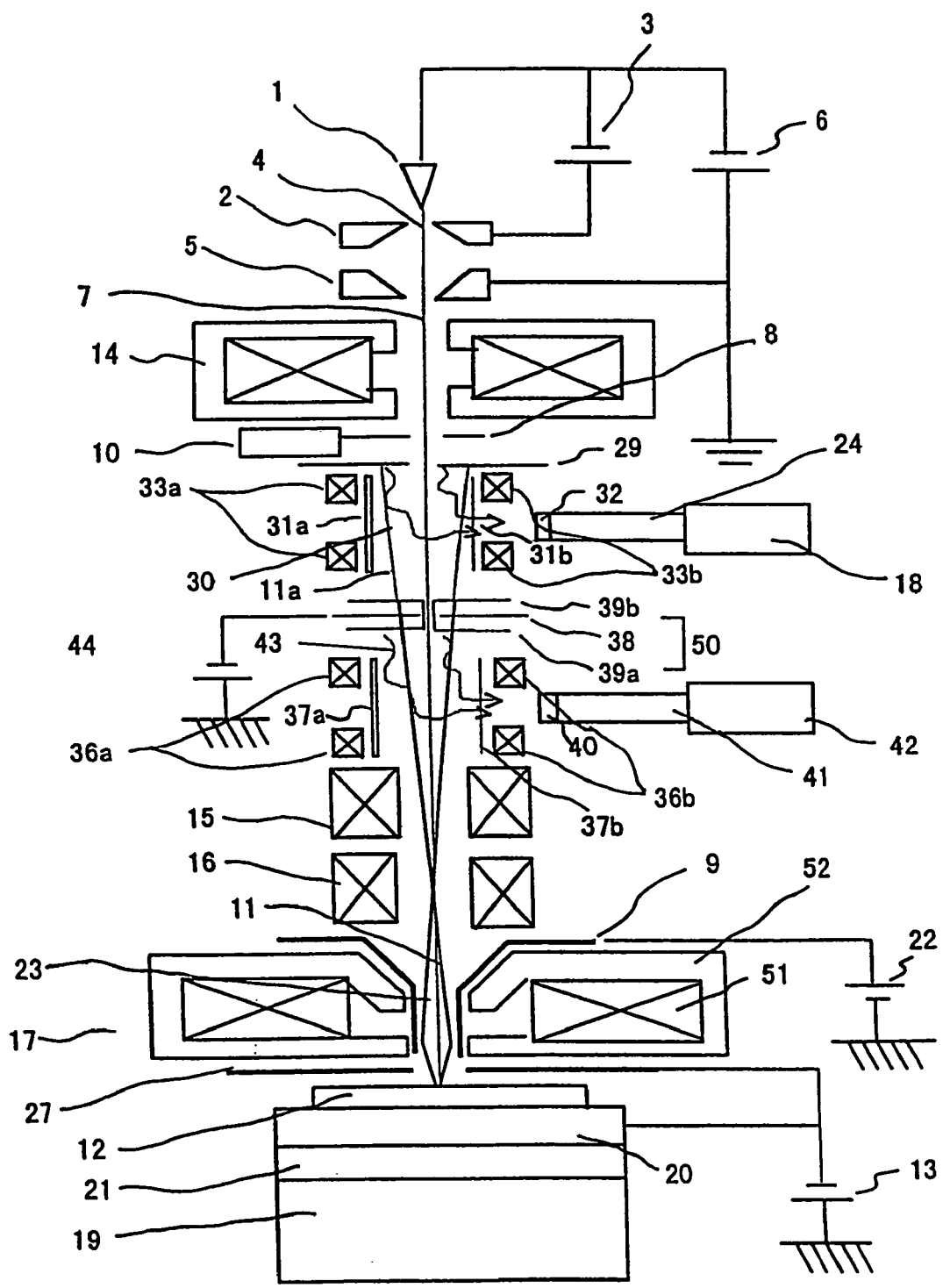
FIG. 10 is a figure showing an example of the energy filter of an embodiment of this invention incorporated into a scanning electron microscope.

Below, a scanning electron microscope which incorporates the energy filter of this embodiment of the invention is explained. FIG. 10 is a summary diagram of the scanning electron microscope.

FIG. 10 is a scanning electron microscope used at low accelerating voltages, such that the secondary electron emission ratio exceeds 1. In particular, a later-stage acceleration method, in which a positive voltage is applied to an accelerating cylinder provided within the objective lens such that high resolution is obtained even at low accelerating voltages, and a retarding method in which a negative voltage is applied to the sample to decelerate the electron beam immediately before the sample, are adopted.

When a pulling-out voltage 3 is applied between the electric field emission cathode 1 and the pulling-out electrode 2, emission electrons 4 are emitted. The emission electrons 4 are further accelerated (or in some cases decelerated) between the pulling-out electrode 2 and the anode 5, which is at ground potential. After passing through the anode 5, the accelerating voltage of the electron beam (primary electron beam 7) matches the electron gun accelerating voltage 6. The primary electron beam 7 undergoes scanning deflection by the condenser lens 14, upper scanning deflector 15, and lower scanning deflector 16.

The deflection intensities of the upper scanning deflector 15 and lower scanning deflector 16 are adjusted such that two-dimensional scanning of the sample 12 is performed, with the lens center of the objective lens 17 as fulcrum. The deflected primary electron beam 7 is accelerated by the later-stage accelerating voltage 22 applied to the accelerating cylinder 9 provided in the path of the objective lens 17. Having undergone later-stage acceleration, the primary electron beam 7 is narrowly focused on the sample 12 by the lens action of the objective lens 17. After passing through the objective lens 17, the primary electron beam 7 is decelerated by a decelerating electric field created between the sample 12, to which a retarding voltage 13 (negative voltage) is applied, and the accelerating cylinder 9, and reaches the sample 12.

As already explained, the decelerating electric field applied between the sample 12 and the accelerating cylinder 9 suppresses the return of secondary electrons to the sample (insulator surface), and also has the effect of raising the voltage at the surface of insulators. In this embodiment, the sum of the regarding voltage 13 applied to the sample and the later-stage accelerating voltage 22 applied to the accelerating cylinder 9 is equivalent to the control voltage 98 of FIG. 5. In this embodiment, 6 kV, which is the sum of the 1 kV retarding voltage and the 5 kV later-stage accelerating voltage, is applied between the sample 12 and the accelerating electrode 9. As a result of application of the 6 kV, the surface of insulators can be electrified to a positive voltage of several tens of volts, and it has been confirmed that secondary electrons within a contact hole are pulled upward extremely efficiently.

The secondary electrons generated at the sample are further accelerated by the retarding voltage, and are impelled toward the detector, so that a high detection efficiency can be obtained. By setting this retarding voltage to an appropriate value, the efficiency of generation of secondary electrons upon collision with the shield mesh 111b can be improved, and the secondary electron detection efficiency can be raised.

In the device of this embodiment of the invention, the sample is surrounded by a holder 20 and by a protective electrode 27 to which the same negative voltage as the holder can be applied, in order to enable the application of an appropriate negative voltage (to form a decelerating electric field) when the sample is covered by an insulating film and a negative voltage cannot be applied directly. By adopting such a configuration, the sample is positioned in a negative electric field region, so that even if a negative voltage cannot be applied directly, a decelerating electric field can be formed based on a prescribed negative potential.

The accelerating voltage of the primary electron beam 7 when it passes through the objective lens 17 is equal to the electron gun accelerating voltage 6 plus the later-stage accelerating voltage 22, which is higher than the accelerating voltage upon final incidence on the sample 12 (the electron gun accelerating voltage 6 minus the retarding voltage 13). As a result, a narrower electron beam (with higher resolution) is obtained compared with the case in which the primary electron beam with the accelerating voltage at which the beam is incident on the sample 12 (the electron gun accelerating voltage 6 minus the retarding voltage 13) is itself focused by the objective lens 17. This is because of a reduction in the lens aberration, and in particular of the chromatic aberration, of the objective lens 17.

In this embodiment, the electron gun accelerating voltage 6 is 2 kV, the later-stage accelerating voltage 22 is 5 kV, and the retarding voltage 13 is 1 kV; the primary electron beam 7 passes through the objective lens 17 at 7 kV, and the accelerating voltage at which it is finally incident on the sample is 1 kV. In this example, the resolution is 3 nm, and improvement to one part in three compared with the 10 nm resolution resulting from focusing at 1 kV.

When the sample 12 is irradiated with the primary electron beam 7, secondary electrons 11 are generated. The secondary electrons in this embodiment include both secondary electrons in the narrow sense, with an accelerating voltage of less than approximately 50 eV, and also reflected electrons.

The electric field applied to the sample acts as an accelerating field for the generated secondary electrons 11, so that the secondary electrons are drawn into the passage of the objective lens 17 (within the accelerating cylinder 9), and the magnetic field of the objective lens 17 causes them to rise, while being acted on by the lens. Secondary electrons 11 which have passed through the objective lens 17 then pass through the scanning deflectors 15, 16.

Secondary electrons 11 which have passed by the scanning deflectors 15, 16 are incident on the energy filter 50. Secondary electrons 11a which have passed through the energy filter 50 (secondary electrons and/or reflected electrons with high energies) collide with the reflecting plate 29. The reflecting plate 29 is a conductive plate having an aperture in the center to allow the primary electron beam 7 to pass. The surface with which secondary electrons 11a collide is of a material with a good secondary electron emission efficiency, such as for example a metal evaporation-deposited surface. The following explanation is for an example in which secondary electrons 11a which have passed through the energy filter are caused to collide with a reflecting plate 29 and detected; however, a configuration may also be employed in which, for example, a scintillator and microchannel plate are positioned in the same position as the reflecting plate to detect secondary electrons 11a.

Secondary electrons 11a which have collided with the reflecting plate 29 generate secondary electrons 30 at this time. The secondary electrons 30 created by the reflecting plate 29 are deflected by an electrostatic deflecting electrode 31a to which a negative voltage is applied and by an electrostatic deflecting electrode 31b to which a positive voltage is applied, relative to ground. The electrostatic deflecting electrode 31b is of mesh shape, such that deflected secondary electrons 30 can pass through. 33a and 33b are magnetic field deflecting coils, which generate a magnetic field orthogonal to the electric field created by the electrostatic deflecting electrodes 31a, 31b, and are adjusted so as to cancel deflection of the primary electron beam 7 by electrostatic deflection.

Secondary electrons which have passed by the mesh-shape electrostatic deflector electrode 31b are drawn toward a scintillator to which a high voltage of +10 kV (not shown) is applied, and collide with the scintillator, to emit light. This light is guided to a photomultiplier tube 18 by a light guide 24, converted into an electrical signal and amplified (first electron detector). Based on the output, CRT brightness modulation (not shown) is performed.

On the other hand, secondary electrons 11 colliding with the shield mesh 39a comprised by the energy filter 50 also generate secondary electrons 43. These secondary electrons 43 are detected by a method similar to that used for secondary electrons 11a which have passed through the energy filter. The secondary electrons are deflected by an electrostatic deflecting electrode 37a to which a negative voltage is applied and an electrostatic deflecting electrode 37a to which a positive voltage is applied, relative to ground. The electrostatic deflecting electrode 37b is of mesh shape, so that deflected secondary electrons 43 can pass through.

36a, 36b are magnetic field deflecting coils, which generate a magnetic field orthogonal to the electric field created by the electrostatic deflecting electrodes 37a, 37b, and cancel the deflection of the primary electron beam 7 by electrostatic deflection. In this way, the second electron detector in the device of this embodiment of the invention comprises deflectors, and detects secondary electrons 43 which have been guided away from the axis of the primary electron beam by the deflectors.

It is desirable that this deflector be provided in a position as close as possible to the shield mesh 39a in order to guide secondary electrons 43 generated by the shield mesh 39a to the second electron detector; but this is not necessary, and there are no restrictions on the position, so long as secondary electrons generated at the shield mesh 39a are properly guided to the detector. Also, as another mode for the second electron detector, a configuration may be employed in which the shield mesh 39a is used as a detector element.

Secondary electrons which have passed by the mesh-shape electrostatic deflecting electrode 37b are drawn toward the scintillator 40, to which a positive high voltage of 10 kV (not shown) is applied; these collide with the scintillator 40, and light is emitted. This light is guided by a light guide 41 to the photomultiplier tube 42 and converted into an electrical signal, which is amplified. Based on this output, CRT brightness modulation (not shown) is performed.

Figure 11:
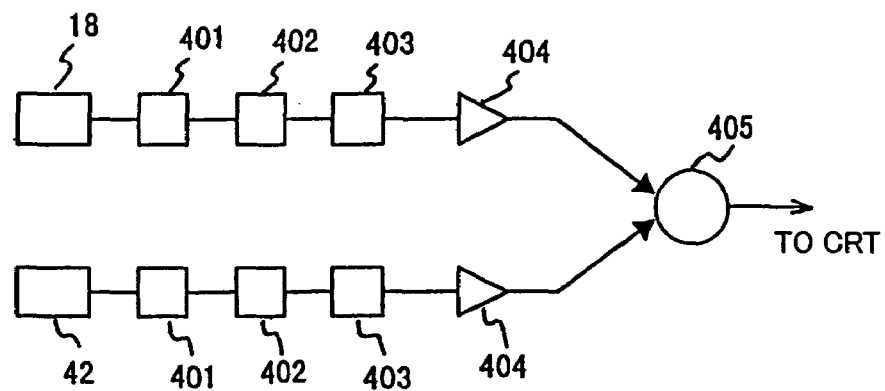
FIG. 11 is a figure showing the progress of processing of output signals of a secondary electron detector.

As shown in FIG. 11, the outputs of the secondary electron detectors 18, 42 are sent to image memory 402 via an A/D converter 401. The data is then sent from the image memory to an amplifier 404 via a D/A converter 403, passes through an adder 405, and CRT brightness modulation is performed. The device of this embodiment of the invention has a control device, not shown, which performs various operations described below, and controls the different components of the scanning electron microscope.

Next, a representative construction of the mesh of the energy filter 50 is explained. Assuming that the transmission ratio of the shield mesh 39a is 50%, and that the transmission efficiency of the filter mesh 38 and shield mesh 39b is 80% or higher, the mesh is assembled in such a way that, as seen from the direction of incidence of secondary electrons 11a, the filter mesh 38 and shield mesh 39b are in the shadow of the shield mesh 39a.

By means of this configuration, 50% of the secondary electrons 11 collide with the reflecting mesh 39a and are detected by the second electron detector, and the remaining 50% are energy-selected by the energy filter 50 and detected by the first electron detector. The shield meshes 39a, 39b of the device of this embodiment of the invention have the advantage of suppressing the effect on primary electrons of the electric field for energy filtering created by the filter mesh 38.

The shield mesh 39a has the advantage of suppressing the unwanted circumstance in which the electric field for energy filtering accelerates secondary electrons generated by collisions with the shield mesh 39a back toward the sample, thus impeding detection by the second electron detector.

Figure 12:
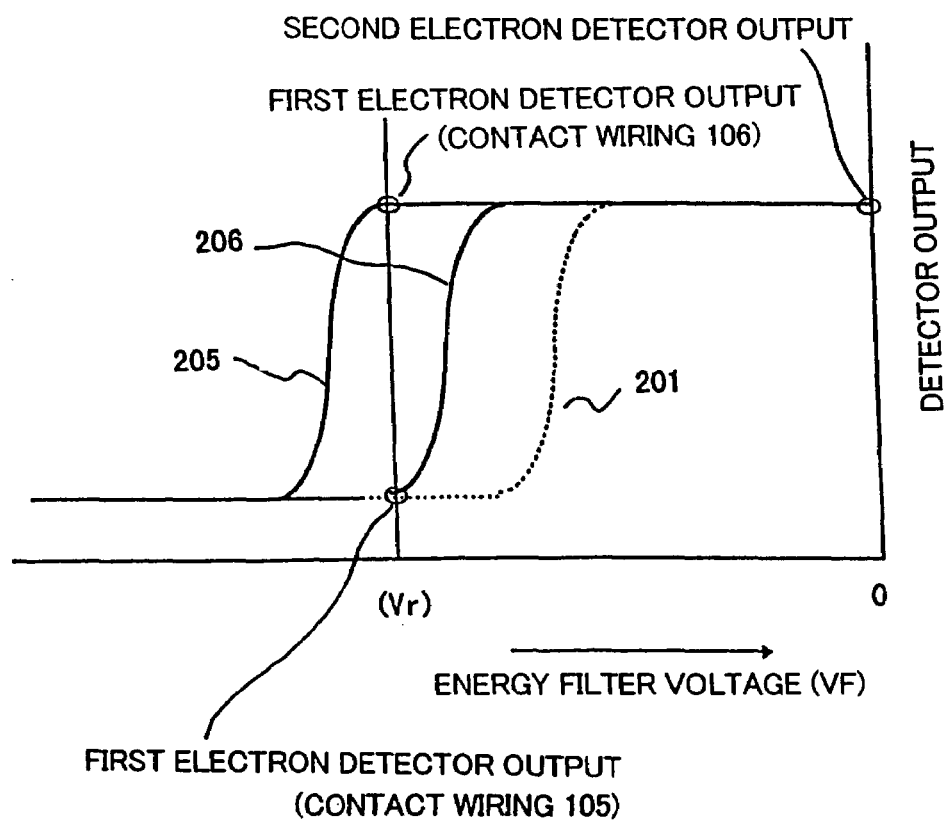
FIG. 12 is a figure showing the amount of output of a detector versus the voltage applied to the energy filter.

Next, signals obtained during operation of the energy filter are explained in detail. FIG. 12 shows the relation between the output of the first electron detector, which detects secondary electrons which have passed through the energy filter, and the filter voltage 44 (VF) applied to the filter mesh 38. The horizontal axis of the graph shows the filter voltage 44, given as a negative voltage.

The curve 205 shows the secondary electrons emitted from the contact wiring 105 of FIG. 3 due to changes in the filter voltage 44. Of the secondary electrons incident on the energy filter 50, secondary electrons at less than 50 eV have an energy substantially equivalent to that of acceleration by the retarding voltage 13 (after emission from the sample, the electrons are accelerated by the retarding voltage 13 and the later-stage accelerating voltage 22, but when leaving the accelerating cylinder 9, are decelerated by the later-stage accelerating voltage 22).

On the other hand, reflected electrons have an energy equivalent to that of the electron gun accelerating voltage 6. Consequently secondary electrons with low acceleration energies can no longer penetrate, starting when the filter voltage 44 is equal to the retarding voltage (Vr), and so the signal begins to decline. When the voltage is set to approximately negative 10 V, the decline stops, and the signal becomes nearly constant. Thereafter the signal is almost entirely due to reflected electrons.

The curve 206 shows changes in the amount of secondary electrons emitted from the contact wiring 106 of FIG. 3 with the filter voltage 44. When the wiring or similar on the sample is broken, positive electrification occurs, and so the decline begins at a lower filter voltage than for the curve 205. For example, if the filter voltage is fixed at Vr, then the detection output is high for curve 205 but low for curve 206, as shown in the figure, and the voltage difference for contact wiring, that is, the difference between normal wiring and defective wiring, appears as a difference in detector output.

The output of the first detection means, which detects secondary electrons which have collided with the shield mesh 39a, is equivalent to a 0 V filter voltage, and the detection output magnitude is the same for 205 and 206.

The curve 201 in FIG. 12 corresponds to secondary electrons from the insulator 101. The curve is shifted to the right because the surface of the insulator 101 is positively electrified. Depending on the intensity of the electric field applied to the sample surface, the static charge voltage on the surface of the insulator may become high, possibly causing discharge within the sample or other problems. For this reason, a method in which, prior to observation, the energy filter voltage is changed as shown in FIG. 12, and the surface potential is determined from changes in the output signal of the first electron detector, is effective. If the surface potential is higher than necessary, the electric field intensity or accelerating voltage can be adjusted, to control the surface potential at a suitable value.

FIG. 13 shows schematically images obtained from the first electron detector and second electron detector when observing contact wiring. In FIG. 13, a) is an image obtained from the first electron detector. Nine contact wiring regions (105, 106) are observed. Because the filter mesh voltage is set to Vr, the defective wiring 106 appears dark (cf. FIG. 12). When this first electron detector is used, wiring with connection faults can be detected.

In FIG. 13, b) is an image obtained based on the output of the second electron detector. This output of the second electron detector depends on the number of secondary electrons, and is unrelated to the energy of the electrons leaving the sample. Because of this, the wiring 106 with a connection fault appears to be the same brightness as the wiring 105 with normal connection. Thus by relying on sample images based on the output from the second electron detector, accurate shape observations (inspections) are possible.

For example, in cases where the shape is faulty, as with the contact wiring 106a, by comparing with the shapes of terminals in the vicinity, anomalous shapes can be detected. In shape detection, repetition of the same pattern is utilized, employing image processing technology. For example, within a semiconductor element there are created numerous memory devices with the same structure. Shape inspection is performed by comparing the basic structure (cells) of these memory devices, or by comparing circuits (chips) created within a wafer.

By means of the device configuration of this embodiment of the invention, it is possible to perform shape inspections and wiring fault inspections together; significant advantages are obtained in improving detection speed and detection accuracy, and sample images based on electrons which have passed through an energy filter with no change with time, as well as sample images based on electrons which have not passed through an energy filter, can be obtained.

When energy filtering is not performed, if a configuration is adopted in which the output of the first electron detector and the output of the second electron detector are merged in order to obtain as many secondary electrons as possible, a detection efficiency comparable to that of a scanning electron microscope without an energy filter can be obtained, even when the scanning electron microscope comprises an energy filter.

Further, even in the case where a negative voltage is applied to the filter mesh 38 and energy filtering is performed, no difference occurs between the output of the second electron detector in this embodiment of the invention in this case, and the output when no energy filtering is performed. Using the second electron detector, the secondary electrons 114a explained using FIG. 9 are detected. By means of the shield mesh 111b, leakage to outside of the electric field formed based on the voltage applied to the filter mesh 113 is suppressed, and so the problem in which secondary electrons which were supposed to collide with the shield mesh 111b being accelerated toward the sample due to this electric field, so that detection by the second electron detector is not possible, can be resolved.

Secondary electrons 114b which have passed through the shield mesh 111b, and which are energy-filtered based on the voltage applied to the filter mesh 113, are accelerated in the sample direction by the filter voltage 110, and so are not detected by the second electron detector.

From the above facts, it is seen that the second electron detector of the device of this embodiment can perform quantitative detection of secondary electrons, without depending on the magnitude of the filter voltage 110. Thus the second electron detector can obtain information suitable for shape inspections of a sample, and due to the quantitative nature of its output, is also suitable for obtaining reference information for use with the output of the first electron detector.

Further, the advantages of the second electron detector (which detects electrons which have not been energy-filtered) of the device of this embodiment are increased further by taking the ratio or the difference with the output of the first electron detector (which detects electrons which have been energy-filtered).

Figure 14:
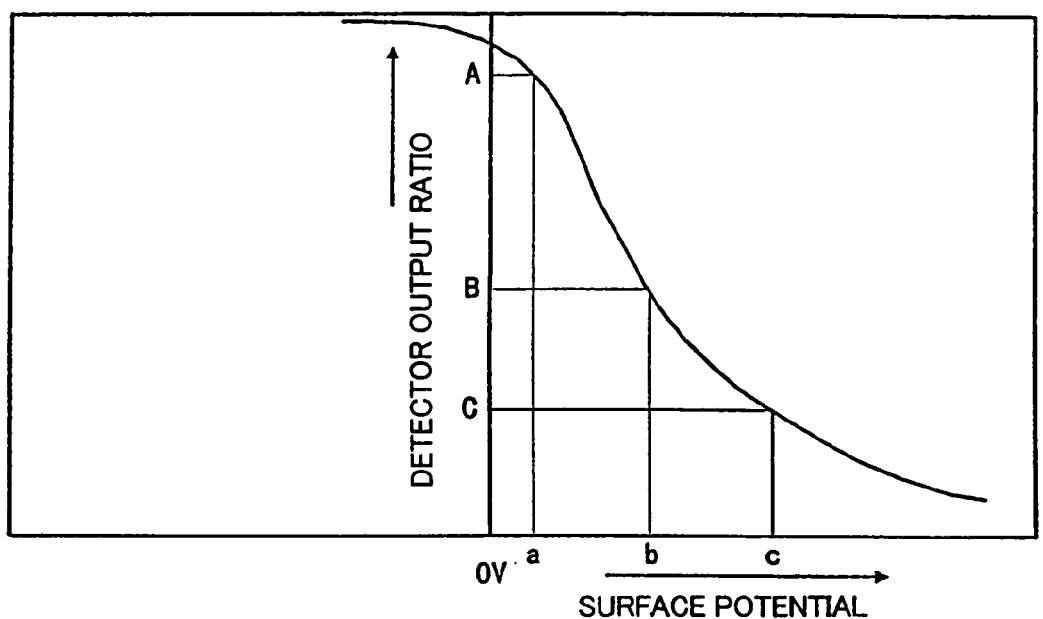
FIG. 14 is a figure showing the output ratio of the detector versus the surface potential of the sample.

In the graph of FIG. 14, the ratio (first electron detector output)/(second electron detector output) is plotted along the vertical axis, and the surface potential of the sample (contact wiring) is plotted along the horizontal axis. The higher the surface potential, the darker the characteristic. The filter voltage 44 applied to the filter mesh can be changed to modify the characteristic. By taking the ratio of the detection outputs, the output is normalized; this curve is constant even if the intensity of the primary electron beam changes. If the sample voltages are a, b and c, there is a one-to-one relationship with the detector output ratios A, B, C.

Figure 15:
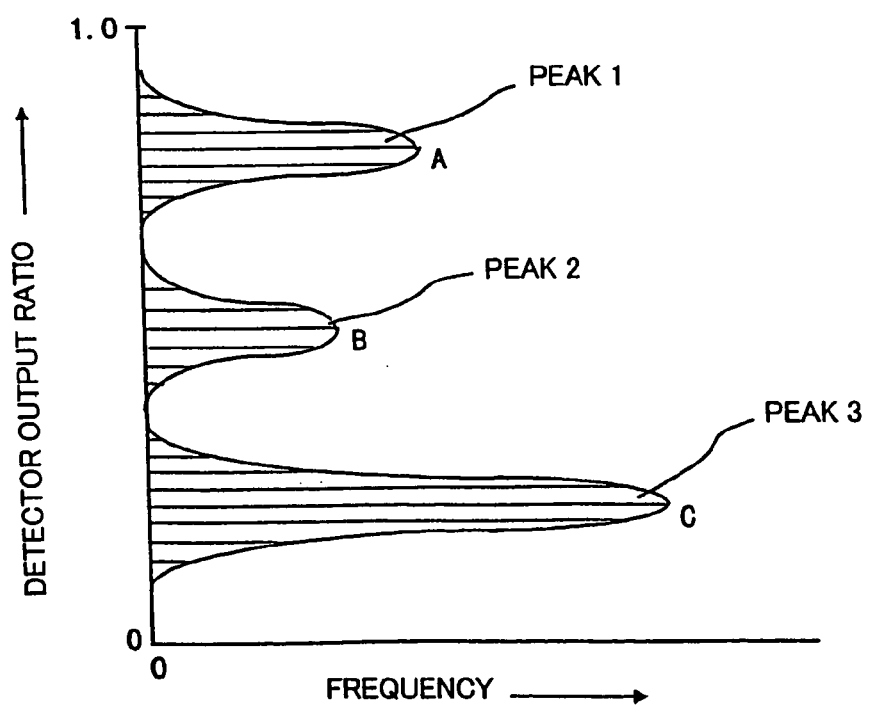
FIG. 15 is a figure showing a method of judging defects using an image frequency distribution (histogram)

FIG. 15 is an example of execution of faulty wiring inspections, using the ratio of detection outputs. The vertical axis shows the ratio (first electron detector output)/(second electron detector output); the horizontal axis indicates the frequency (number of pixels). For example, if the frequency distribution with respect to the detector output ratio is created for an observed image, three peaks may appear, as for example in the figure. Peak 1 is pixels corresponding to well-connected wiring (bright wiring) 105, peak 2 is pixels corresponding to faulty wiring (dark wiring) 106, and peak 3 is pixels corresponding to the surrounding insulation. The presence of peak 2 indicates that there exists faulty-connection wiring; by extracting this portion, it is possible to detect (produce as an image) only the faulty wiring portions.

Extraction of this characteristic portion can be performed by selecting pixels having a particular characteristic brightness, or within a particular characteristic range of brightnesses, excluding all other pixels, and displaying the result. Specifically, a first threshold value A is provided below a peak, and only pixels brighter than this are selected. A second threshold value B is provided, and pixels brighter than this are excluded, and the result displayed. Through this selection, only peaks, that is, only pixels equivalent to faulty wiring portions can be displayed.

Figure 19:
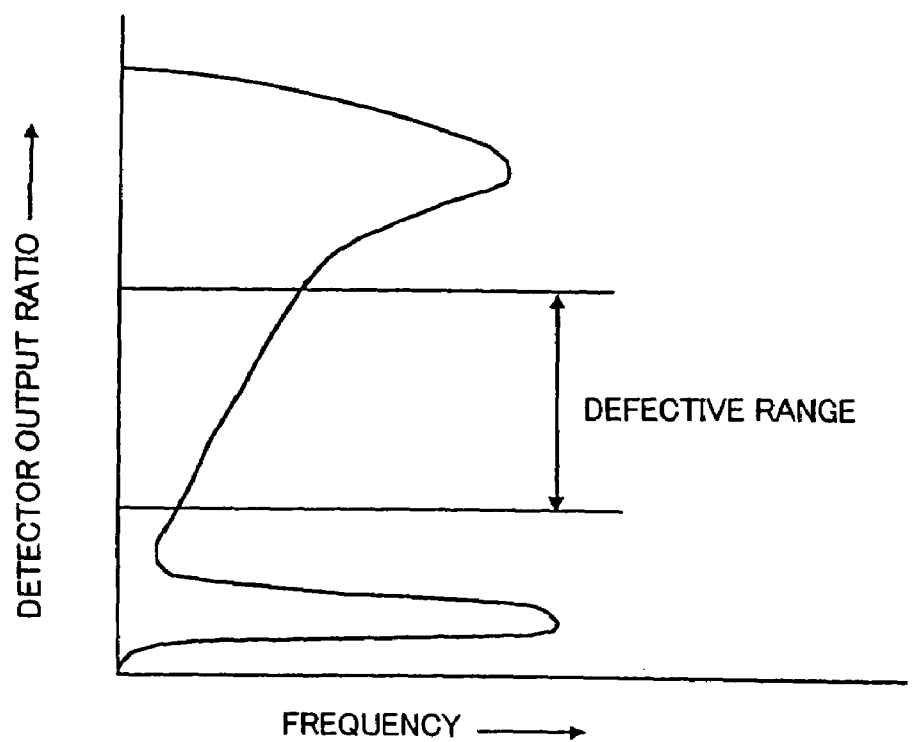
FIG. 19 is a figure showing another method for judging defects using a histogram.

Using only the output of the first electron detector, judgment is difficult when all wiring portions are normal, or when all wiring portions are faulty. However, by using the ratio of outputs, even if all portions are normal or all wiring portions are faulty, reliable judgment is possible. Even in cases where the extent of the defect is distributed, such as shown in FIG. 19, by determining a range for the ratio of detection outputs, it is possible to stipulate normal and defective portions.

In FIG. 15, the value obtained by dividing the area of the peak 2 by the sum of the areas of peak 1 and peak 2 is the defect rate (whereas if the area of peak 1 is divided by the sum of the areas of peak 1 and peak 2, the normal rate is obtained). When the presence or absence of wiring connection faults, or a percentage, is as a figure in evaluations, this method is useful. It is also sufficient to output only a normal:defective ratio, without computing the defect rate. By using such a figure for evaluations in, for example, management of the production yield of semiconductor wafers, uniform and accurate yield management can be performed.

Figure 16:
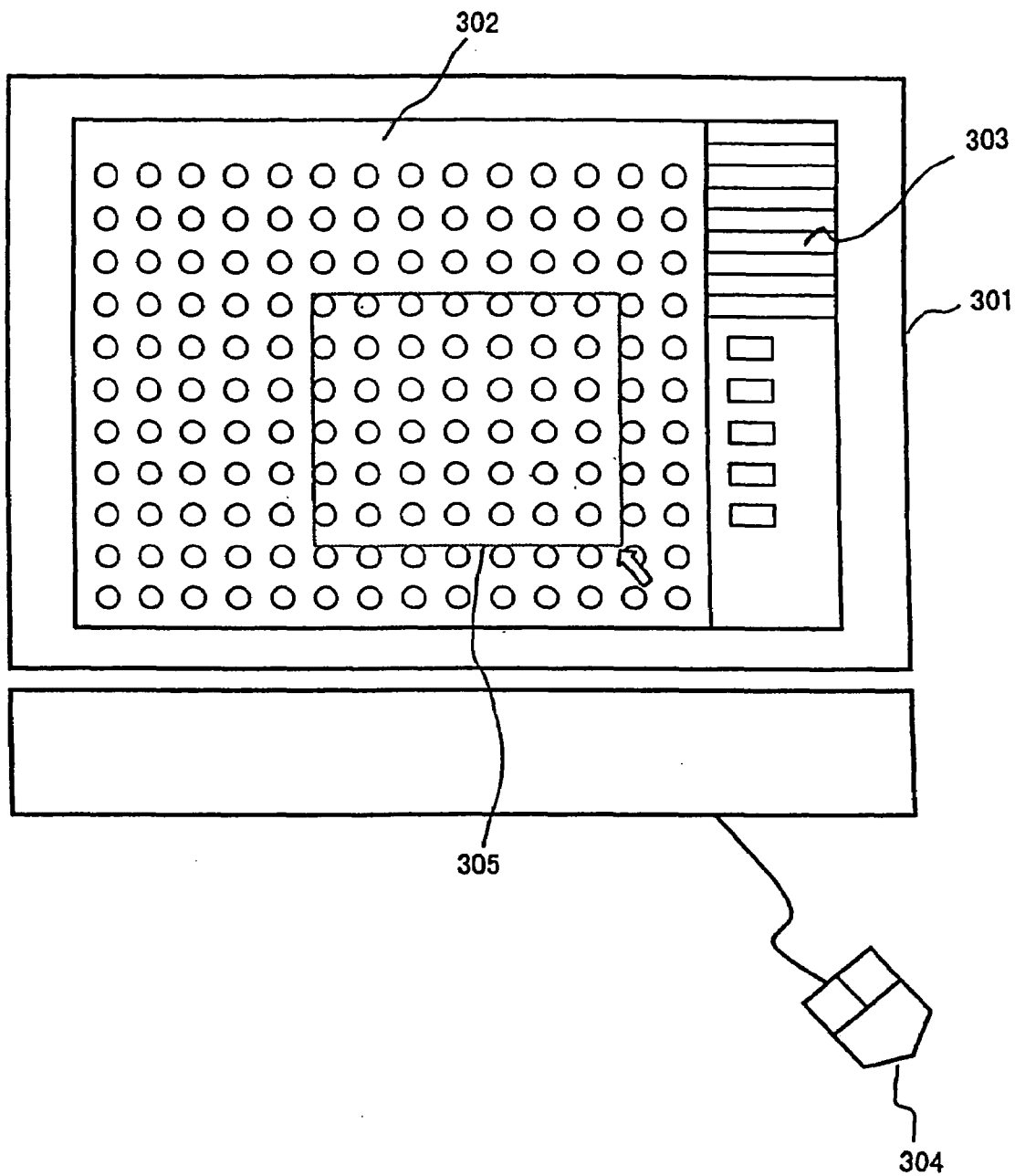
FIG. 16 is a figure showing an example of a display device in an embodiment of this invention.

FIG. 16 is a figure showing an example of a display device in a device suitable for computation of the defect rate. The display device 301 displays a display area showing the optical conditions and similar of the scanning electron microscope, and a sample image display area 302. Numerous contact wiring regions are displayed in the sample image display area 302. The pointing device 304 is used to set a rectangular region 305 in the sample image display area 302. By performing the computations described above within this rectangular region, the defect rate and other figures can be computed for a region selected by the operator.

Using the above method using a detector output ratio, it is possible to inspect for faulty wiring connections using conditions in which the electron beam is not narrowly focused, that is, by planar irradiation of the range for inspection by an electron beam. Here the electron beam irradiation may be performed by fixed irradiation of the inspection range with a planar electron beam; or, the inspection range may be scanned by an electron beam. In this inspection, the filter mesh voltage Vf is varied, and the ratio of the first electron detector output and the second electron detector output is taken.

Figure 17:
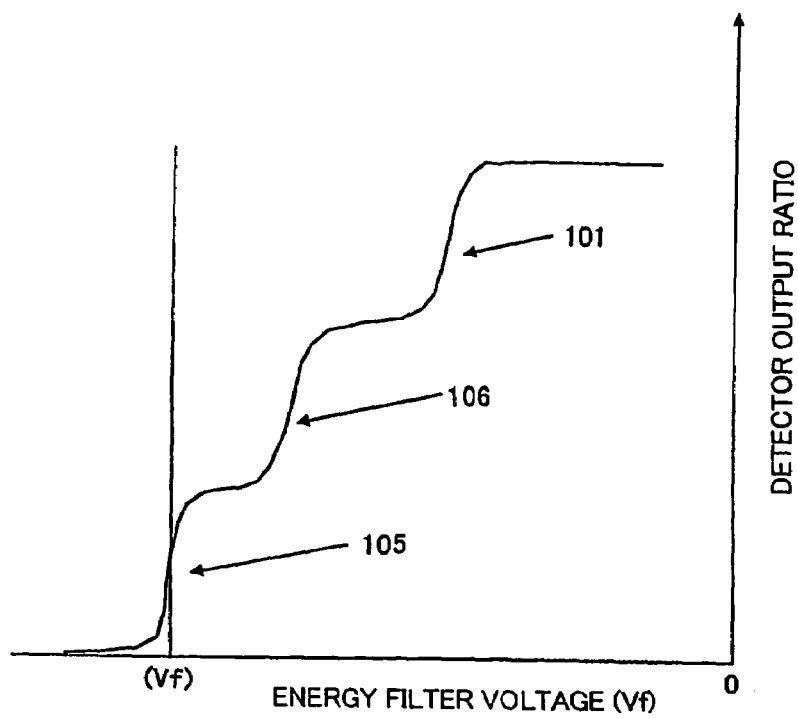
FIG. 17 is a figure showing changes in the detector output ratio obtained when the energy filter voltage is changed.

FIG. 17 shows changes in the detector output ratio (vertical axis) obtained when the energy filter voltage (Vf, horizontal axis) is changed. The steps indicated by the arrows in the figure represent secondary electrons emitted from normally-connected wiring 105, defective wiring 106, and surrounding insulation 101 (separated due to differences in the secondary electron energies).

Figure 18:
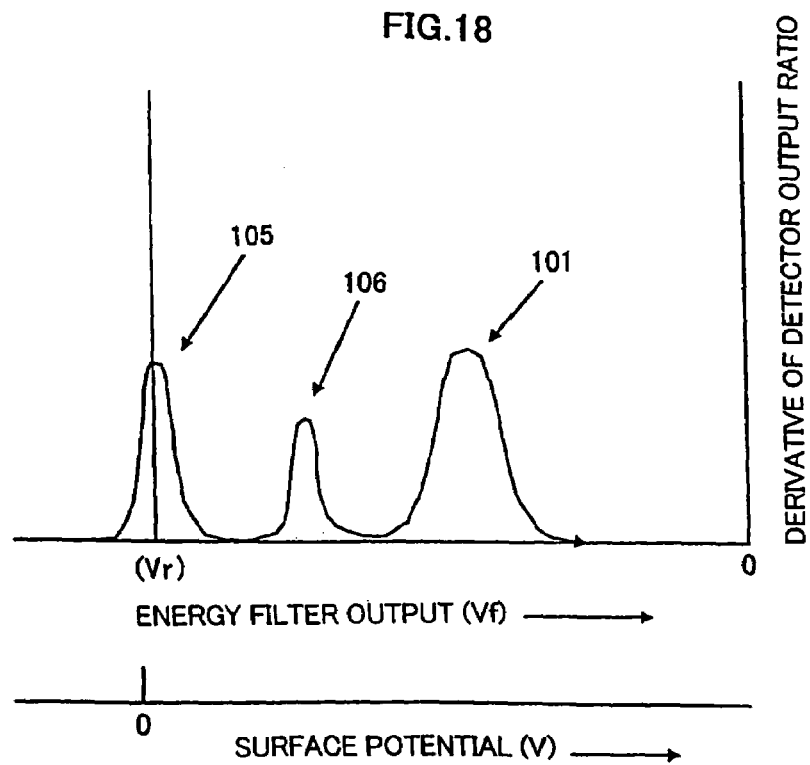
FIG. 18 is a figure showing the result of differentiation of the changes of FIG. 17.

FIG. 18 is the result of differentiation of the curve of FIG. 17. More easily observed peaks are obtained corresponding to the normally-connected wiring 105, defective wiring 106, and surrounding insulation 101. The energy filter voltage can be converted into a surface voltage. The voltage Vr shown in the figure is equivalent to a surface potential of 0 V. From this distribution, the existence of defective areas can be determined. Here, the peak 106 indicates a defect. In actual inspections, evaluations and judgments are performed based on the existence of specific surface potential peaks, or on comparison with the distribution obtained from a normal region.

Because in this method there is no need to narrowly focus the electron beam, irradiation with a large-current electron beam is possible. As a result, rapid inspections can be performed. It is also possible to switch between large-current irradiation and scanning of a narrowly focused electron beam if necessary.

The above explanation has assumed application in inspections of contact wiring for connection defects; however, application to inspections of contact hole apertures, or absence of apertures, is similarly possible. When an energy filter is used, a contact hole with an aperture appears bright, since the substrate can be seen, whereas a contact hole that does not have an aperture (is not open) appears dark, due to positive electrification of the remaining insulator, and so can be easily identified.

Another example of utilization of the detector of this invention is explained. For example, without operating the energy filter of the first electron detector (Vf is set to 0 V), the sum of the outputs of the first electron detector and the second electron detector is taken. In this state, nearly 100% of the secondary electrons can be utilized.

Also, by simultaneously or selectively displaying the sample image based on the output of the first electron detector, the sample image based on the output of the second electron detector, and the image computed (by addition, subtraction, or similar) from the outputs of both detection means, various features of the sample can be evaluated.

In FIG. 10, 8 is a diaphragm which controls the aperture angle of the primary electron beam 7, and axial alignment can be performed using the adjustment knob 10. 19 is an XY movement mechanism to move the sample 12 in the XY directions; on this is placed a holder 20 insulated by the insulating plate 21, and a retarding voltage 13 is applied. The sample (for example, a wafer) is placed on this holder 20. Placement on the holder enables electrical connection, and the retarding voltage 13 can also be applied to the sample 12.

Figure 20:
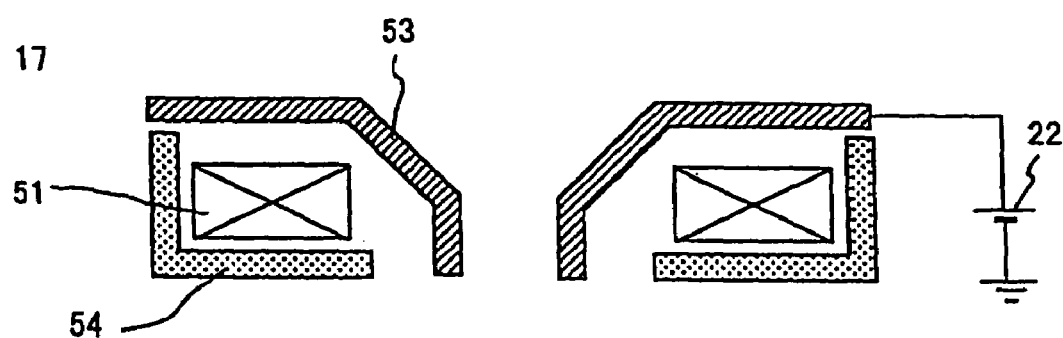
FIG. 20 is a figure showing another working device, in which the magnetic path of the objective lens is divided and a later-stage accelerating voltage is applied; and, FIG. 21 is a figure which explains another embodiment of the energy filter.

In the embodiment of FIG. 10, the objective lens 17 comprises a magnetic path 52 and coil 51, and an accelerating cylinder 9 is positioned within the path of the objective lens 17. FIG. 20 is an example in which the structure of the objective lens 17 is different; the magnetic path is separated into an upper magnetic path 53 and a lower magnetic path 54. The upper magnetic path 53 is insulated from ground, so that a later-stage accelerating voltage 22 can be applied. In this configuration, compared with methods in which an accelerating cylinder 9 is positioned within the objective lens 17 as in the embodiment of FIG. 10, the mechanical precision is good, and higher performance can be obtained.

Figure 21:
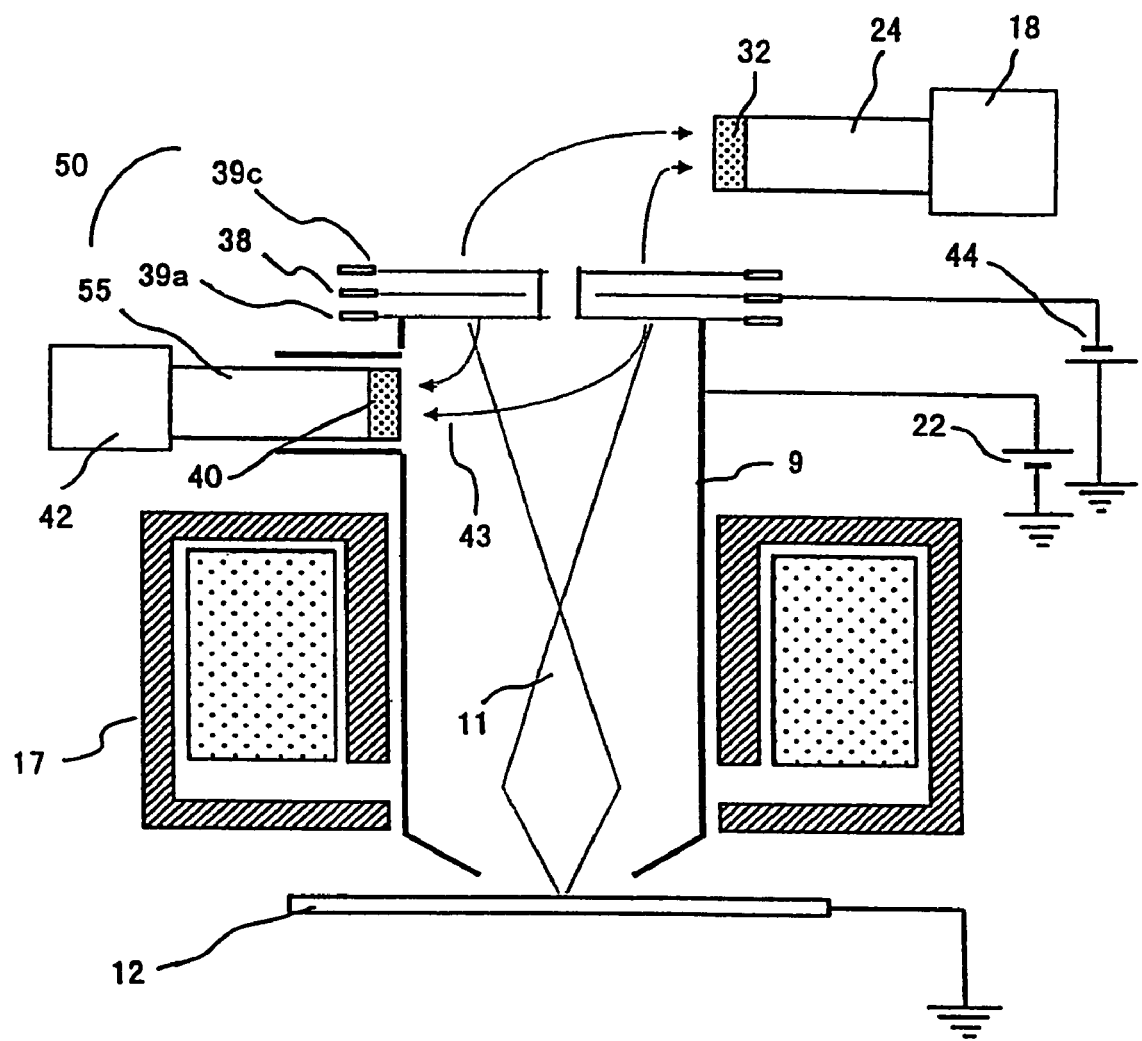

FIG. 21 shows another embodiment of this invention. In the embodiment of FIG. 10, secondary electrons are incident on the energy filter with an energy equivalent to the retarding voltage applied to the sample 12. That is, application of the retarding voltage 13 is a necessary condition. FIG. 21 is an embodiment of this invention in which a voltage is not applied to the sample. Secondary signals are drawn into the accelerating cylinder 9 by a later-stage accelerating voltage 22 applied to the accelerating cylinder 9.

An energy filter 50 is positioned on the opposite side of the accelerating cylinder 9 from the sample 12. The energy filter 50 comprises a filter mesh 38, shield mesh 39b, and reflecting mesh 39a. The same later-stage accelerating voltage 22 applied to the accelerating cylinder 9 is applied to the reflecting mesh 39a and shield mesh 39b. Secondary electrons 43 created by collisions of secondary electrons 11 with the reflecting mesh 39a are drawn by a high voltage (10 kV) applied to the scintillator 40, causing the scintillator 40 to emit light, which passes through a light guide 41, is amplified by a photomultiplier tube and detected.

Here, a simple method is described employing electrostatic deflectors 37a, 37b, or combining electrostatic deflectors 37a, 37b with electromagnetic deflectors 36a, 36b, and which does not use an ExB deflector. A filter voltage 44 which discriminates energies is applied to the filter mesh 38 of the energy filter 50. Secondary electrons which have passed through the energy filter 50 are drawn by a high voltage (10 kV) applied to the scintillator 32 provided above the energy filter 50, causing the scintillator to emit light, which passes through the light guide 24, is amplified by a photomultiplier tube and detected.

Below also, a simple method is described employing electrostatic deflectors 37a, 37b, or combining electrostatic deflectors 37a, 37b with electromagnetic deflectors 36a, 36b, and which does not use an ExB deflector, is described.

In this embodiment, reflected electrons cannot be detected by the first electron detector. A reflecting plate at the same potential as the accelerating cylinder 9 may be provided above the energy filter, so that secondary electrons which have passed through the energy filter 50 are caused to collide with the reflecting plate, and the newly created secondary electrons are detected. In this method, when the energy filter is used to shut out secondary electrons, it is possible to detect only reflected electrons. In this embodiment, the accelerating cylinder 9 is integrated with the energy filter 50; but a construction may also be adopted in which a voltage is applied to the upper magnetic path of the objective lens, a cylinder at this same potential is provided, and an energy filter is mounted on the upper portion of this cylinder, as shown in FIG. 20. It is also possible to extend the upper magnetic path to the reflecting plate, in a construction in which secondary electrons which have passed through the energy filter are detected by the reflecting plate.

Using this device, it is possible to inspect either an entire wafer, or specified regions thereof; but the data of defect inspection equipment can be used, employing light or electrons to specify locations to be observed or inspected, in order to execute inspections more efficiently. Review and classification of electrical connection defects can be executed employing an image based on the output of the second electron detector, an image based on the output of the first electron detector, or employing the ratio of outputs of both detectors.

Embodiments of this invention have been explained in terms of a scanning electron microscope; but application to other charged particle beam devices is also possible. Also, the various computations and processing explained in these embodiments can be performed by a computation device or similar which is separate from the scanning electron microscope. In this case, publicly known information transmission media may be used for input of information obtained using the scanning electron microscope to the computation device.

By means of this invention, it becomes possible to simultaneously execute inspections of external appearance and inspections of electrical connections using a low-accelerating voltage scanning electron microscope, and as a result a new application for scanning electron microscopes with low accelerating voltages is created.

In these embodiments, examples in which two detectors are used have been described. Examples of the public disclosure of two detectors in a scanning electron microscope appear in International Examined Patent No. WO99/46798, Japanese Patent Laid-open No. 9-171791 (U.S. Pat. No. 5,872,358), Japanese Patent Laid-open No. 9-507331 (U.S. Pat. No. 5,493,116), and Japanese Patent Laid-open No. 7-192679 (U.S. Pat. No. 5,608,218).

What is claimed is:

1. A scanning electron microscope comprising:
   an electron source;
   a focusing lens for focusing a primary electron beam emitted by said electron source; and
   an energy filter for energy-filtering an electron emitted from a sample, said scanning electron microscope further comprising:
   a first detector for detecting electrons indicating an electric potential contrast of the sample; and
   a second detector for detecting electrons indicating a shape of the sample.

2. The scanning electron microscope according to claim 1, further comprising a control apparatus for calculating a ratio of an output of said first detector to that of said second detector as an energy-filtering voltage is varied.

3. The scanning electron microscope according to claim 1, further comprising an accelerating tube disposed between said energy filter and said sample for accelerating said primary electron beam.

4. The scanning electron microscope according to claim 1, further comprising an accelerating tube disposed between said energy filter and said sample for accelerating said primary electron beam, wherein a voltage-applying member is provided for drawing secondary electrons towards said first and second detectors in said accelerating tube.

5. The scanning electron microscope according to claim 1, further comprising a negative-voltage applying power source for applying a negative voltage to said sample.

6. The scanning electron microscope according to claim 1, wherein said energy filter includes a filter mesh to which a negative voltage is applied, and a shield mesh disposed between said filter mesh and said sample.

7. The scanning electron microscope according to claim 6, wherein said filter mesh is located in the shade of said shield mesh when seen from said sample.

8. A scanning electron microscope comprising:
an electron source;
a focusing lens for focusing a primary electron beam emitted by said electron source; and
an energy filter for energy-filtering an electron emitted from a sample, said scanning electron microscope further comprising:
a first detector for detecting electrons indicating an electric potential contrast of the sample;
a second detector for detecting electrons indicating a shape of the sample; and
a control unit for calculating the ratio of or a difference in outputs of said first and said second detectors.

9. A method of detecting electrons by scanning a sample with an electron beam, said method comprising separating the electrons into those that indicate a potential contrast of the sample and those that indicate a shape of the sample, using an energy filter.

* * * * *